United States Patent
Kane et al.

(10) Patent No.: US 6,273,854 B1
(45) Date of Patent: Aug. 14, 2001

(54) MEDICAL DIAGNOSTIC ANALYSIS METHOD AND SYSTEM

(75) Inventors: Edward Kane; Patricia C. Kane, both of Millville, NJ (US)

(73) Assignee: Body Bio Corporation, Millville, NJ (US)

( * ) Notice: Subject to any disclaimer, the term of this patent is extended or adjusted under 35 U.S.C. 154(b) by 0 days.

(21) Appl. No.: 09/072,603

(22) Filed: May 5, 1998

(51) Int. Cl.$^7$ .................................................. A61B 5/00
(52) U.S. Cl. ............................................................ 600/300
(58) Field of Search .......................... 705/2, 3; 600/300, 600/301

(56) References Cited

U.S. PATENT DOCUMENTS

| | | | |
|---|---|---|---|
| 4,290,114 | 9/1981 | Sinay | 364/900 |
| 4,731,725 | 3/1988 | Suto et al. | 364/415 |
| 4,733,354 | 3/1988 | Potter et al. | 364/415 |
| 5,023,785 | 6/1991 | Adrion et al. | 364/413.08 |
| 5,075,101 * | 12/1991 | Siguel | 424/9 |
| 5,088,314 * | 2/1992 | Takashi | 600/532 |
| 5,255,187 | 10/1993 | Sorensen | 364/413.02 |
| 5,315,505 | 5/1994 | Pratt et al. | 364/633.01 |
| 5,427,101 * | 6/1995 | Sachs et al. | 600/534 |
| 5,437,278 | 8/1995 | Wilk | 128/653.1 |
| 5,463,548 | 10/1995 | Asada et al. | 364/413.02 |
| 5,594,638 | 1/1997 | Iliff | 395/203 |
| 5,642,731 | 7/1997 | Kehr | 128/630 |
| 5,704,350 | 1/1998 | Williams, III | 128/630 |
| 5,746,204 | 5/1998 | Schauss | 128/630 |
| 5,954,640 * | 9/1999 | Szabo | 600/300 |
| 5,967,994 * | 10/1999 | Wang | 600/509 |
| 5,993,386 * | 11/1999 | Ericsson | 600/300 |

FOREIGN PATENT DOCUMENTS

WO 97/20496  6/1997 (WO).

\* cited by examiner

*Primary Examiner*—Robert L. Nasser
(74) *Attorney, Agent, or Firm*—Drinker, Biddle & Reath LLP

(57) ABSTRACT

The present invention provides a system and method for medical diagnostic analysis. The system includes a computer system for storing a plurality of databases. The databases maintain medical research data regarding analyte characteristics and bodily function characteristics. A first database maintains a plurality of analyte records, wherein each record holds information regarding a particular analyte that was determined from the results of testing a human test group. Each analyte record includes a low value, a high value and a mode value. A second database maintains a plurality of bodily function records wherein each bodily function record includes analytes associated with the particular bodily function and an analyte level indicative of the bodily function. The method matches an individual's bodily fluid laboratory results with the databases to identify supportive nutrient metabolic agents for each of the analytes within a lab report, potential negative drug reaction as to each analyte, and disease pattern matching depicting historical disease patterns as they pertain to the individual's analyte status.

35 Claims, 20 Drawing Sheets

BASIC STATUS REPORT

FATTY ACID RED CELL MEMBRANE DATE: 7/7/97

THE % STATUS IS THE WEIGHTED DEVIATION OF THE LABORATORY RESULT.

| | %STATUS | | RESULT | LOW | HIGH |
|---|---|---|---|---|---|
| 16DMA | 106.67 | H | 1.50 | 1.03 | 1.33 |
| 18:0 DMA | -4.55 | | 2.21 | 2.01 | 2.45 |
| 18:1 DMA | 4.88 | | 0.59 | 0.14 | 0.96 |
| ADRENIC C22:4w6 | -82.09 | L | 1.85 | 2.28 | 3.62 |
| ALPHA LINOLENIC C18:3w3 | -14.29 | | 0.18 | 0.03 | 0.45 |
| ARACHIDIC C20:0 | 5.56 | | 0.32 | 0.22 | 0.40 |
| ARACHIDONIC C20:4w6 | -109.90 | L | 11.36 | 12.51 | 14.43 |
| BEHENIC C22:0 | 1.19 | | 1.37 | 0.94 | 1.78 |
| CAPRIC C10:0 | 0.00 | | 0.00 | -0.01 | 0.01 |
| CAPROLEIC C10:1 | -50.00 | L | 0.00 | 0.00 | 0.01 |
| CAPRYLIC C8:0 | 0.00 | | 0.00 | -0.01 | 0.01 |
| DIHOMO-Y LINO. C20:3w6 | -49.29 | L | 1.06 | 1.05 | 2.45 |
| DIMORPHECOLIC C18:2w3t | -20.00 | | 0.06 | 0.00 | 0.20 |
| DOCOSAHEXA, C22:6w3 | 103.88 | H | 6.49 | 2.92 | 5.24 |
| DOCOSAPENTA, C22:5w3 | 79.76 | H | 2.65 | 1.56 | 2.40 |
| DOCOSAPENTA, C22:5w6 | 25.00 | | 0.86 | 0.53 | 0.97 |
| EICOSADIENOIC C20:2w6 | -108.33 | L | 0.13 | 0.20 | 0.32 |
| EICOSANOIC C20:1w7 | 33.33 | H | 0.13 | 0.03 | 0.15 |
| EICOSAPENTA, C20:5w3 | 212.07 | H | 1.80 | 0.28 | 0.86 |
| ELAIDIC C18:1w9t | 100.00 | H | 0.42 | 0.00 | 0.28 |

IMPACT OF AGING

FIG. 4A

BASIC STATUS REPORT

IMPACT OF AGING  FATTY ACID RED CELL MEMBRANE  DATE: 7/7/97

THE % STATUS IS THE WEIGHTED DEVIATION OF THE LABORATORY RESULT.

| | %STATUS | | RESULT | LOW | HIGH |
|---|---|---|---|---|---|
| PALMITOLEIC C16:1w7 | −90.00 | L | 0.13 | 0.25 | 0.55 |
| PENTACOSANOIC C25:0 | 30.00 | H | 0.11 | 0.03 | 0.13 |
| PENTADECANOIC C15:0 | 366.67 | H | 0.31 | 0.06 | 0.12 |
| PHYTANIC | −33.33 | L | 0.01 | 0.00 | 0.06 |
| PRISTANIC | 60.00 | H | 0.12 | 0.01 | 0.11 |
| STEARIC C18:0 | 8.00 | | 14.55 | 13.68 | 15.18 |
| TRANSVACCENIC C18:1w7t | −35.11 | L | 0.57 | 0.43 | 1.37 |
| TRICOSANOIC C23:0 | 25.00 | H | 0.29 | 0.20 | 0.32 |
| TRIDECANOIC C13:0 | 250.00 | H | 0.06 | 0.00 | 0.02 |
| UNDECANOIC C11:0 | 1250.00 | H | 0.25 | −0.01 | 0.01 |
| VACCENIC C18:1w7 | −176.92 | L | 0.50 | 0.83 | 1.09 |
| TOTAL STATUS DEVIATION | 95.65 | | | | |
| TOTAL STATUS SKEW | 42.61 | | | | |

FIG. 4A (Cont'd)

IMPACT OF AGING
PATIENT ID:

PATIENT ID:

BASIC STATUS REPORT
FATTY ACID RED CELL MEMBRANE DATE:

THE % STATUS IS THE WEIGHTED DEVIATION OF THE LABORATORY RESULT.

LOW RESULTS

| | %STATUS | RESULT | LOW | HIGH |
|---|---|---|---|---|
| VACCENIC C18:1w7 | −176.92 L | 0.50 | 0.83 | 1.09 |
| ARACHIDONIC C20:4w6 | −109.90 L | 11.36 | 12.51 | 14.43 |
| EICOSADIENOIC C20:2w6 | −108.33 L | 0.13 | 0.20 | 0.32 |
| MYRISTOLEIC C14:w5 | −108.33 L | 0.00 | 0.07 | 0.19 |
| HEXACOSANOIC C26:0 | −104.55 L | 0.07 | 0.13 | 0.24 |
| MEAD C20:3w9 | −100.00 L | 0.05 | 0.07 | 0.11 |
| PALMITOLEIC C16:1w7 | −90.00 L | 0.13 | 0.25 | 0.55 |
| ADRENIC C22:4w6 | −82.09 L | 1.85 | 2.28 | 3.62 |
| GAMMA LINOLENIC C18:3w6 | −66.67 L | 0.01 | 0.04 | 0.22 |
| CAPROLEIC C10:1 | −50.00 L | 0.00 | 0.00 | 0.01 |
| ERUCIC C22:1w9 | −50.00 L | 0.04 | 0.04 | 0.06 |
| DIHOMO-Y LINO C20:3w6 | −49.29 L | 1.06 | 1.05 | 2.45 |
| NONADDECANOIC C19:0 | −40.00 L | 0.03 | 0.02 | 0.12 |
| TRANSVACCENIC C18:1w7t | −35.11 L | 0.57 | 0.43 | 1.37 |
| PHYTANIC | −33.33 L | 0.01 | 0.00 | 0.06 |
| LINOLEIC C18:2w6 | −28.83 L | 10.86 | 10.17 | 13.43 |
| OLEIC C18:1w9 | −28.82 L | 10.59 | 10.23 | 11.93 |
| HENEICOSANOIC C21:0 | −25.00 L | 0.03 | 0.01 | 0.09 |

BASIC STATUS REPORT

PATIENT WITH DEPRESSION  BLOOD TEST DATE: 12/18/96

THE % STATUS IS THE WEIGHTED DEVIATION OF THE LABORATORY RESULT.

| | %STATUS | | RESULT | LOW | HIGH |
|---|---|---|---|---|---|
| A/G RATIO | 98.25 | H | 2.58 | 0.80 | 2.00 |
| ALBUMIN | 44.44 | H | 4.90 | 3.20 | 5.00 |
| ALKALINE PHOSPHATASE | 26.19 | L | 45.00 | 20.00 | 125.00 |
| ANION GAP | 18.00 | | 10.80 | 4.00 | 14.00 |
| B.U.N. | -33.33 | L | 10.00 | 7.00 | 25.00 |
| B.U.N./CREATININE RATIO | -23.10 | | 11.11 | 6.00 | 25.00 |
| BASOPHIL COUNT | -50.00 | L | 0.00 | 0.00 | 200.00 |
| BASOPHILS | -50.00 | L | 0.00 | 0.00 | 3.00 |
| BILIRUBIN,TOTAL | -11.54 | | 0.50 | 0.00 | 1.30 |
| CALCIUM | -5.56 | | 9.30 | 8.50 | 10.30 |
| CALCIUM/PHOSPHORUS RATIO | -28.65 | L | 2.51 | 2.30 | 3.30 |
| CHLORIDE | 57.69 | H | 109.00 | 95.00 | 108.00 |
| CHOLESTEROL | -80.00 | L | 104.00 | 140.00 | 260.00 |
| CO2 | -33.33 | L | 22.00 | 20.00 | 32.00 |
| CREATININE | -21.43 | | 0.90 | 0.70 | 1.40 |
| EOSINOPHIL COUNT | 32.40 | H | 462.00 | 50.00 | 550.00 |
| EOSINOPHILS | 50.00 | H | 6.00 | 0.00 | 6.00 |
| FREE T4 INDEX(T7) | 4.17 | | 2.70 | 1.40 | 3.80 |
| GGT | -36.67 | L | 6.00 | 0.00 | 45.00 |
| GLOBULIN | -65.00 | L | 1.90 | 2.20 | 4.20 |

FIG. 4C

PATIENT WITH DEPRESSION

BASIC STATUS REPORT

BLOOD TEST DATE: 12/18/96

THE % STATUS IS THE WEIGHTED DEVIATION OF THE LABORATORY RESULT.

| | %STATUS | | RESULT | LOW | HIGH |
|---|---|---|---|---|---|
| GLUCOSE | -7.78 | | 89.00 | 70.00 | 115.00 |
| HDL | -48.95 | L | 36.00 | 35.00 | 130.00 |
| HEMATOCRIT | -36.36 | L | 36.50 | 35.00 | 46.00 |
| HEMOGLOBIN | -32.86 | L | 12.60 | 12.00 | 15.50 |
| IRON, TOTAL | -37.59 | L | 43.00 | 25.00 | 170.00 |
| LDH | -6.80 | | 108.00 | 0.00 | 250.00 |
| LDL | -58.82 | L | 56.00 | 62.00 | 130.00 |
| LYMPHOCYTE COUNT | 2.03 | | 2541.00 | 850.00 | 4100.00 |
| LYMPHOCYTES | 0.00 | | 33.00 | 18.00 | 48.00 |
| MCH | 46.88 | H | 32.81 | 27.00 | 1.33 |
| MCHC | 13.01 | | 34.52 | 32.00 | 36.00 |
| MCV | 25.26 | | 95.05 | 80.00 | 100.00 |
| MONOCYTE COUNT | 4.78 | | 693.00 | 200.00 | 1100.00 |
| MONOCYTES | 50.00 | H | 9.00 | 0.00 | 9.00 |
| NEUTROPHIL COUNT | -10.25 | | 4004.00 | 1500.00 | 7800.00 |
| NEUTROPHILS | -34.00 | L | 52.00 | 48.00 | 73.00 |
| PHOSPHORUS | 10.00 | | 3.70 | 2.50 | 4.50 |
| POTASSIUM | -33.33 | L | 3.80 | 3.50 | 5.30 |
| PROTEIN, TOTAL | -18.00 | | 6.80 | 6.00 | 8.50 |

FIG. 4C (Cont'd)

BASIC STATUS REPORT

PATIENT WITH DEPRESSION  
BLOOD TEST DATE: 12/18/96

THE % STATUS IS THE WEIGHTED DEVIATION OF THE LABORATORY RESULT.

| | %STATUS | | RESULT | LOW | HIGH |
|---|---|---|---|---|---|
| R.B.C. | 54.62 | | 3.84 | 3.90 | 5.20 |
| SGOT | -19.05 | L | 13.00 | 0.00 | 42.00 |
| SGPT | -25.00 | L | 12.00 | 0.00 | 48.00 |
| SODIUM | -22.73 | L | 138.00 | 135.00 | 146.00 |
| SODIUM/POTASSIUM RATIO | 35.96 | H | 36.32 | 26.00 | 38.00 |
| T-3 UPTAKE | 26.92 | H | 32.00 | 22.00 | 35.00 |
| THYROXINE (T4) | -2.50 | | 8.30 | 4.50 | 12.50 |
| TRIGLYCERIDES | 26.00 | | 60.00 | 0.00 | 250.00 |
| UTRA-SENSITIVE TSH | -28.43 | L | 1.50 | 0.40 | 5.50 |
| URIC ACID | -64.00 | L | 1.80 | 2.50 | 7.50 |
| W.B.C. | 5.71 | | 7.70 | 3.80 | 10.80 |
| TOTAL STATUS DEVIATION | 31.15 | | | | |
| TOTAL STATUS SKEW | -10.13 | | | | |

FIG.4C (Cont'd)

MEDICAL DIAGNOSTIC ANALYSIS METHOD AND SYSTEM

FIELD OF THE INVENTION

The present invention relates generally to automated medical diagnosis systems and methods for performing medical diagnostic analysis, and more particularly to such systems and methods that compare patient diagnostic data with predetermined ranges of specific analyte values to provide a disease diagnosis and suggested or contraindicated treatment strategies.

BACKGROUND OF THE INVENTION

Medical research in the second half of the 20th century has produced, and continues to produce, an ever increasing body of knowledge. The complexity and interrelationships of various diseases and the analytes that may be detected in various diagnostic tests for diseases are more than sufficient to tax the capacity of most medical practitioners. To aid medical practitioners in disease diagnosis, computerized expert systems have been developed to collate medical diagnostic data with various diseases to guide physicians in prescribing treatments for their patients. Such prior art medical diagnostic systems do not adequately provide a framework for analyzing the individual patient's diagnostic results to collate such results into a disease analyte pattern. Furthermore, such systems do not address therapeutic and/or contraindicated treatment strategies.

One method, described in PCT Publication Number WO 97/20496, uses the mean value of human experience test results to determine a presence level of a particular indicator for an individual. The use of the mean value does not provide an accurate determination of whether an individual's indicator levels are within a normal range.

SUMMARY OF THE INVENTION

The present invention is a computerized medical diagnostic system and method. The system and method are used analyze and diagnose an individual's analyte levels. An "analyte" is any substance that is quantified or detected by an experimental procedure. In order to perform the analysis and diagnosis, the individual is tested to determine an analyte value for the various analytes found in their body. The test may be performed through various methods, such as through drawing and testing blood, urine or other bodily fluids. The results of the testing provide analyte values for each of the analytes for the individual.

The system of the present invention, as illustrated in FIG. 1, includes a computer 100 including at least a central processing unit (CPU) 102 and a storage medium 104. The storage medium 104 may be, for example, a hard disk drive. The system may also include an input device 106, for example a keyboard, a mouse or a disk drive and an output device 108, for example a monitor or a printer. The system includes a first database stored on the storage medium. The first database maintains analyte data information, in the form of analyte values, for a plurality of analytes. The first database includes a plurality of analyte records, wherein each record holds information regarding a particular analyte that was determined from the results of testing a human test group in the same manner the individual was tested to determine the individual's analyte values. Each analyte record includes an analyte low value, an analyte high value and an analyte mode value. The system also includes a second database stored on the storage medium. The second database maintains disease data information, in the form of diseases and associated analytes, for a plurality of diseases. The second database includes a plurality of disease records, wherein each record holds information regarding a particular disease. Each disease record includes a set of analytes associated with a particular disease. Each analyte of the analyte set has an associated analyte level. The analyte level is indicative of the particular disease. Once the databases are stored on the storage medium, an individual's analyte values are then input to the CPU and compared with the first database data to determine a presence levels for each analyte for the individual. The presence level is the relative amount of a particular analyte present in the individual in comparison to the human test group. Thereafter the presence levels are compared with the second database data to determine disease pattern matches associated with the various analyte presence levels.

The analyte presence level for an individual may be affected by many environmental and/or personal factors such as age, sex, race, pregnancy, residence location, previous or current diseases, previous or current drug usage, etc., all of which are factors to be considered in creating an accurate analysis system. The present invention provides a method for correlating such factors with the various test analytes to identify therapeutic and/or contraindicated treatments and drugs.

The present invention provides a method for automated analysis of an individual's analyte values to provide increased accuracy in disease identification.

The present invention also provides increased accuracy in automated disease identification systems by determining analyte presence levels for use in the disease identification analysis.

The present invention further provides an automated medical diagnostic database system wherein an individual's analyte values are automatically categorized as high, normal or low for increased accuracy in disease determination.

The present invention still further provides an automated medical diagnostic database system wherein analyte test results are combined in various panels to provide diagnostic information regarding various bodily conditions and functions.

The present invention also provides an automated medical diagnostic database system wherein diagnostic data in the form of analyte values gathered from testing the individual on a first date and data also in the form of analyte values gathered from subsequently testing the individual on a second date can be compared to provide information regarding the change in the individual's medical health and the effectiveness of an ongoing medical treatment program.

The present invention further provides an automated medical diagnostic database system wherein the known effects of various drugs and other nutritional-biochemical elements can be utilized to better analyze an individuals health status, and to identify therapeutic and/or contraindicated drugs and elements.

The present invention still further provides an automated medical diagnostic database system wherein the effects of personal and/or environmental factors such as age, sex, pregnancy, residence location, prior or current diseases and drug usage, may be utilized to provide a more accurate medical health analysis.

These and other features and advantages of the present invention will become well understood upon reading the following detailed description of the invention.

DESCRIPTION OF THE DRAWINGS

FIGS. 4A–4C are examples of basic status reports generated by the present invention;

DESCRIPTION OF THE INVENTION

Figure 1:
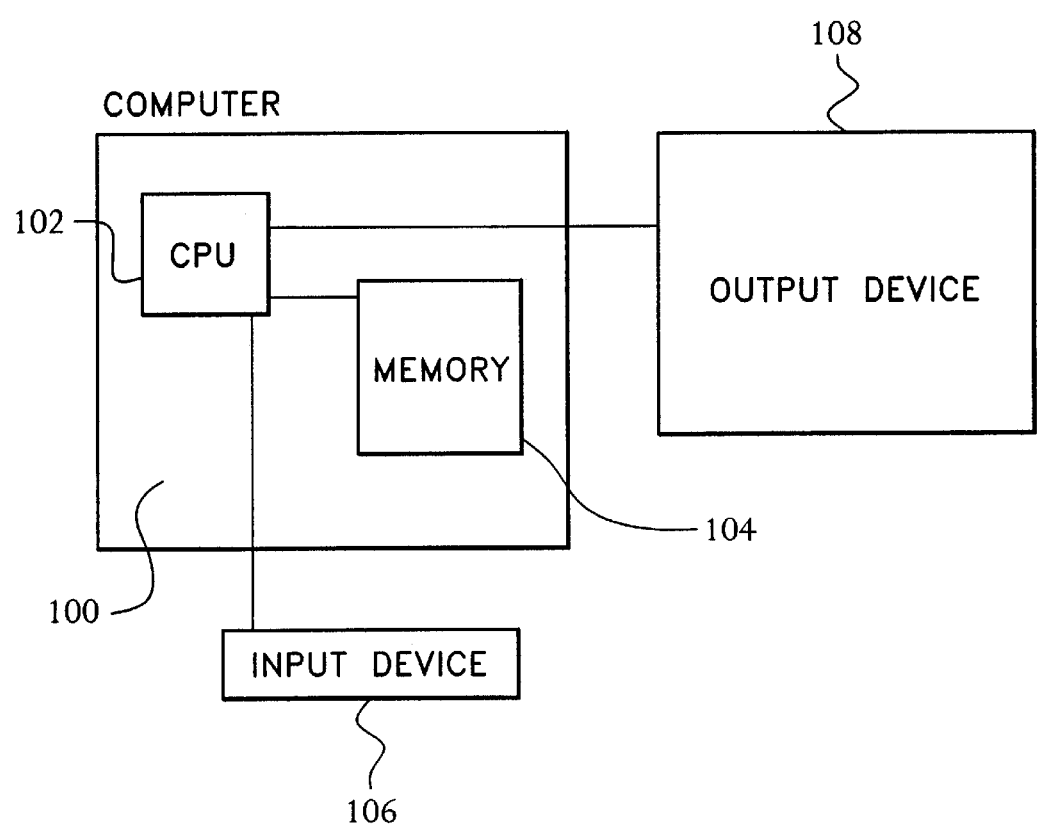
FIG. 1 is a block diagram illustrating the basic system of the present invention.

The system of the present invention may be implemented through hardware, software or any combination of the two. As illustrated in FIG. 1, the system of the present invention includes a computer 100 housing a CPU 102 and a storage medium 104, also known as a memory device. The system may operate under control of a control program or application written to implement the method of the present invention. The control program includes source code instructions that direct the operation of the CPU 102 and the other elements of the system. The control program may be stored in the memory device 104 or the CPU 102.

The method of the present invention involves the analysis of an individual's analyte values, obtained from testing the individual's blood or other bodily fluids to determine the analyte presence level for each of the individual's analytes and then compare the individual's analyte presence levels with a set of known analyte presence levels for various diseases to determine the likelihood that an individual might have particular ones of the diseases. The method is basically accomplished in six steps which are depicted in FIG. 2 and described below.

Figure 2:
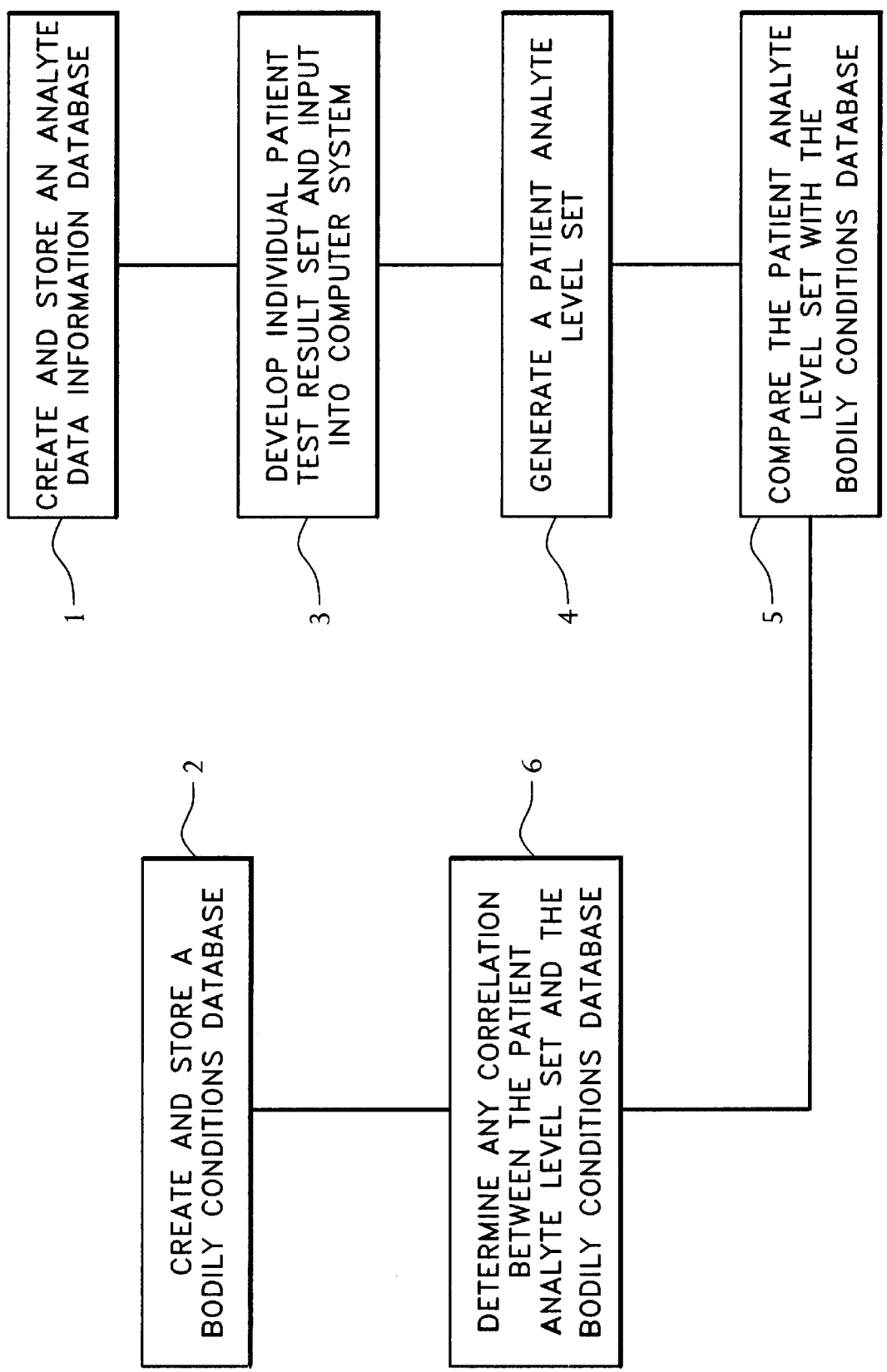
FIG. 2 is a block diagram illustrating the basic method of the present invention.
Figure 3:
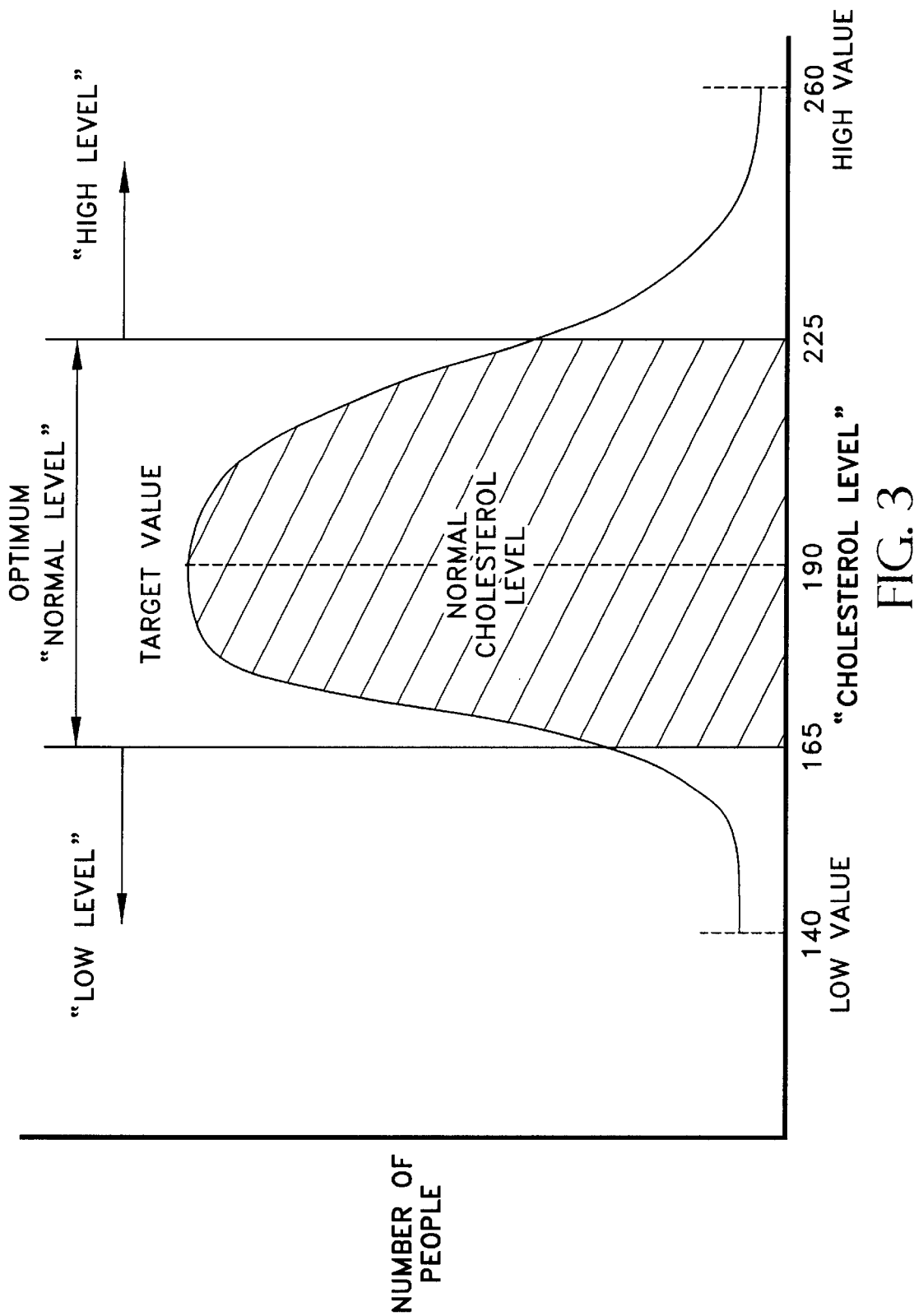
FIG. 3 is a graph illustrating a manner in which High, Low and Normal levels of an analyte are determined in conjunction with the present invention.

FIG. 2 is a block diagram setting forth the various steps in the analytical disease indication method of the present invention. In step 1, a first database is created and stored in a storage medium. The first database maintains analyte data information for a plurality of analytes determined from a statistical analysis of analyte values obtained through testing a human test group, as described above. Table 1 is representative of the first database. In a preferred embodiment, the first database includes an analyte low value, an analyte high value and an analyte mode value for each analyte. As illustrated in FIG. 3, a graph shows a statistical analysis for a particular analyte, cholesterol in this example. This plot is representative of the analyte values obtained from the human test group for the analyte cholesterol. The horizontal axis indicates the cholesterol value. The vertical axis the number of individuals in the human test group that had a particular cholesterol value. In this example, the high value is 260, the low value is 140 and the mode value is 190. The high and low values are determined as two standard deviations of the results generated from the human test group for the particular analyte, in this instance, cholesterol. The mode value is the analyte value that has the greatest number of people from the human test group with that value. In other words, the mode value is the analyte value at the highest point of the curve representative the results from the human test group for a particular analyte. Because the greatest number of people in the human test group have the mode value for their analyte value, the mode value is considered the optimum value for an individual. Therefore, the practitioner will act to drive the individual's analyte values to the mode value. In order to drive the individual's analyte values to the mode value, the practitioner must be able to work from an individual's analyte levels that are a function of the mode value. The present invention provides the system and method for providing analyte levels of this type. This is discussed in more detail below.

TABLE 1

| ANALYTE | LOW VALUE | HIGH VALUE | MODE VALUE |
| --- | --- | --- | --- |
| 1 | 25 | 150 | 90 |
| 2 | 5 | 26 | 14 |
| 3 | 8.5 | 10.8 | 9.6 |
| 4 | 96 | 109 | 103 |
| 5 | 1.9 | 3.5 | 2.6 |
| 6 | 3.90 | 9.0 | 4.7 |
| 7 | 0 | 240 | 170 |
| 8 | 3.3 | 4.5 | 3.5 |
| 9 | 140 | 260 | 190 |
| . | . | . | . |
| . | . | . | . |
| . | . | . | . |

Referring again to FIG. 2, in step 2 a second database is created and stored in the storage medium. The second database maintains disease data information for a plurality of diseases. Table 2 is representative of the second database. In a preferred embodiment, the second database includes data for a plurality of diseases. A group of specific analytes is associated with each disease. An analyte level is associated with each analyte of the analyte group for a particular disease. Analyte levels are denominated as Low (L), High (H) and Normal (N). The analyte levels associated with the disease are indicative of the particular disease. For example, the group of analytes associated with disease D2 includes analytes 1, 3, 6 and 8. Each analyte of this group is characterized an associated analyte level. For disease D2, analyte 1 is L, analyte 3 is L, analyte 6 is L, and analyte 8 is L.

TABLE 2

| DISEASE (1, 2, 3, . . .) | ANALYTES (1, 2, 3, 4, 5, 6, 7, 8, 9, . . .) |
|---|---|
| 1 | 1H, 2L, 7L, 9H, |
| 2 | 1L, 3L, 6L, 8L, |
| 3 | 2H, 3L, 5L, 7H, |

By way of specific example, Table 3 describes three specific diseases, acute myocardial infarction, acquired hemolytic anemia and acromegaly, with related analytes. There are, of course, many diseases and several significant analytes for each, and medical research daily discovers, new diseases and derives new analytes for particular diseases. Thus, step 2 actually comprises a tabulation of known medical research of diseases and the analyte levels indicative of those diseases.

TABLE 3

ACUTE MYOCARDIAL INFARCTION

Analytes

High levels: Alkaline Phosphate, Cholesterol, Creatinine, GGT, LDH, WBC, Neutrophils, Triglycerides, BUN, Uric Acid
Normal
Low levels: Albumin, Iron, Sodium

ACQUIRED HEMOLYTIC ANEMIA (AUTOIMMUNE)

Analytes

High levels: SGOT, SGPT, Basophils, Total Bilirubin, Creatinine, LDH, Monocytes, Phosphorus, BUN, Uric Acid
Normal levels: none
Low levels: Hematocrit, Hemoglobin

ACROMEGALY

Analytes

High levels: Alkaline Phosphatase, Calcium, Creatinine, Glucose, Phosphorus, Potassium, Sodium, BUN
Normal levels: none
Low levels: none Table 4 presents a typical tabulation of some known analytes with test results to provide added understanding by way of specific example. These test results and human experience high, low and mean are derived from known in medical research, and step 2 thus comprises a database of known medical research.

TABLE 4

| ANALYTE | RESULT | LOW VALUE | HIGH VALUE | MODE VALUE | % STATUS | PRESENCE LEVEL |
|---|---|---|---|---|---|---|
| 1. Alkaline Phosphatase | 68 | 25 | 150 | 0 | −17 | N |
| 2. B.U.N. | 9 | 5 | 26 | 14 | −21 | N |
| 3. Calcium | 9.3 | 8.5 | 10.8 | 9.6 | −14 | N |
| 4. Chloride | 108 | 96 | 109 | 103 | 42 | H |
| 5. Globulin | 2.0 | 1.9 | 3.5 | 2.6 | −43 | L |
| 6. Uric Acid | 6.0 | 3.9 | 9.0 | 4.7 | 15 | N |
| 7. Lactate Dehydrodenase | 222 | 0 | 240 | 170 | 37 | H |
| 8. Phosphorus | 3.3 | 2.5 | 4.5 | 3.5 | −10 | N |
| 9. Cholesterol | 160 | 140 | 260 | 190 | −30 | L |
| . | . | . | . | . | . | . |
| . | . | . | . | . | . | . |

Figure 4A:
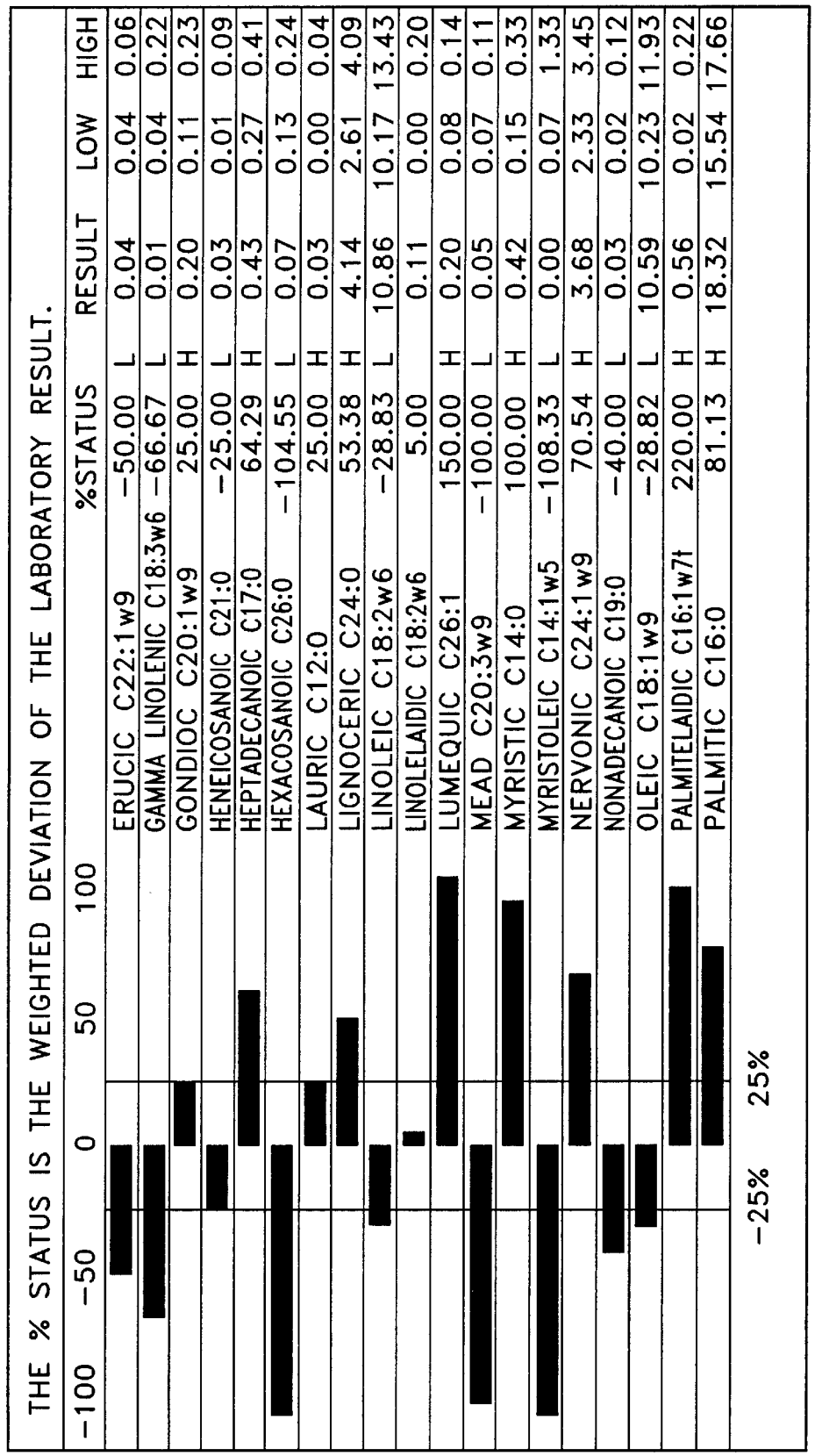
Figure 4B:
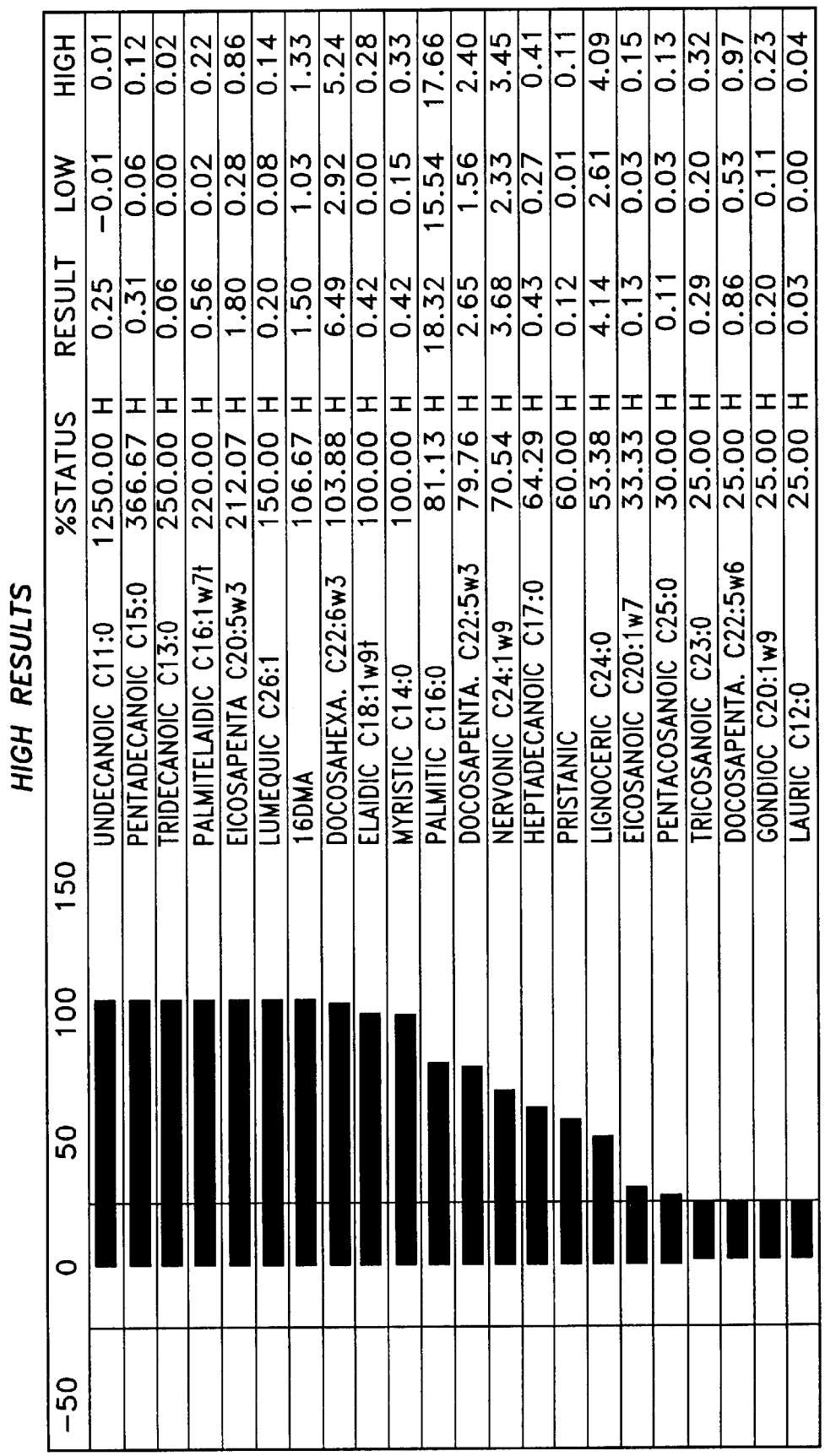

Referring again to FIG. 2, the particular individual's analyte values are input to the CPU, in step 3. According to the present invention, the individual's analyte values are determined from testing blood, serum, urine or other bodily fluids. The collected data may be formatted as a basic status report indicating the individual's analyte values. Examples of such basic status reports are illustrated in FIGS. 4A–14C. A patient test result set includes an analyte value for each of the plurality of analytes maintained in the first database. In a first embodiment, the analytes in the first database are red cell membrane fatty acids, as exemplified in FIG. 4A. The individual's bodily fluid is tested for this group of analytes and the patient test result set includes an analyte value for each of the analytes. In a second embodiment, the analytes in the first database are blood analytes, as exemplified in FIG. 4C. The individual's bodily fluid is tested for this group of analytes and the patient test result set includes an analyte value for each of the analytes. Each analyte value of the patient test result set is an appropriate numerical value indicative of the individual's analyte value. Table 5 illustrates an individual's patient test result set. This table contains 9 analytes. This is meant only to illustrate the set and not to limit the number of possible analytes that may be tested. The patient test result set is also included as the second column in Table 4.

TABLE 5

PATIENT TEST RESULTS

| ANALYTE | 1 | 2 | 3 | 4 | 5 | 6 | 7 | 8 | 9 |
|---|---|---|---|---|---|---|---|---|---|
| RESULT | 68 | 9 | 9.3 | 108 | 2.0 | 6.0 | 222 | 3.3 | 160 |

In step 4 of the method of the present invention a patient analyte level set including an analyte level for each analyte value in the patient test result set is generated using the information maintained in the first database. In a preferred embodiment of the present invention, the analyte level set is generated by first generating a percent status set. The percent status set includes a value for each analyte value in the patient test result set. The percent status value is indicative of a relationship between the individual's analyte values and the test group's analyte values. The percent status set is generated by calculating a percent status value for each analyte value in the patient test result set. The percent status is calculated using one of the following equations:

if the individual's analyte value is greater than the analyte mode value than, $$\% \text{ Status} = 50*(\text{patient test result analyte value} - \text{analyte mode value})/(\text{analyte high value} - \text{analyte mode value})$$

if the individual's analyte value is less than the analyte mode value than, $$\% \text{ Status} = 50*(\text{patient test result analyte value} - \text{analyte mode value})/(\text{analyte mode value} - \text{analyte low value})$$

Table 6 presents the results of calculating the percent status for each of the analyte values of the patient test result set presented in Table 5. The percent status results are also presented in Table 4 for easy comparison with the other parameters.

TABLE 6

| ANALYTE | 1 | 2 | 3 | 4 | 5 | 6 | 7 | 8 | 9 |
|---|---|---|---|---|---|---|---|---|---|
| % STATUS | −17 | −21 | −14 | 42 | −43 | 15 | 37 | −10 | −30 |
| PRESENCE LEVEL | N | N | N | H | L | N | H | N | L |

By determining the percent status as a function of the analyte mode value and changing the denominator of the above referenced equations based upon the relationship of the individual's analyte value and the mode, the percent status provides a very accurate and true picture of the individual's analyte level relative to the most common value for the analyte, as indicated by the mode value. This is in contrast to prior attempts to compare the individual's analyte values to human test group analyte values. In the past, the comparison between the individual's analyte values and the human test group analyte values utilized the mathematical average between the low value and the high value, also known as the mean. The use of the mean value instead of the mode value presents the following potential drawback. If the results of the human test group present a symmetrical bell curve, than the mean value and the mode value will be the same. However, if the human test group does not present a symmetrical bell curve, than the mean value will not equal the mode value. In this instance, the mean value will merely represent a mathematical average between the low value and the high value. This value will not be representative of the most common human value for the particular analyte. As such, any analysis based upon the mean value will suggest to the practitioner to drive the individual's analyte values to a mathematical average and not to the optimum human values, as indicated by the human test group results and the resultant mode value.

Once the percent status set is generated, the percent status result for each analyte is compared to a preselected high status value and a preselected low status value. This comparison forms the basis for determining the individual's analyte level for each particular analyte relative to the test group. In a preferred embodiment of the present invention, the preselected low status value is −25 and the preselected high status value is 25. For all of the percent status set elements having a value less than or equal to −25, the corresponding elements of the patient analyte level set are labeled LOW. For all of the percent status set elements having a value greater than −25 but less than 25, the corresponding elements of the patient analyte level set are labeled NORMAL. For all of the percent status set elements having a value greater than or equal to 25, the corresponding elements of the patient analyte level set are labeled HIGH.

Table 6 presents the results of step 4, wherein an "L" represents a LOW level presence, an "N" represents a NORMAL level presence and a "H" represents a HIGH level presence of the various analytes. For further understanding, the patient analyte level presence of step 4 (L, N or H) are also presented in Table 4.

By generating the patient analyte level set based upon a percent status value that is a function of the mode value for the particular analyte, a practitioner will be better able to adjust the individual's analyte levels towards a normal, optimal human condition. In other words, the use of the mode value provides an analyte offset or percent status relative to the analyte value of the most common human analyte level. By using the offset relative to the mode value in prescribing a course of action, the practitioner is better able to drive the individual's analyte values to the mode values, these values being considered the optimum values.

In step 5 of the method of the present invention, the patient analyte level set is compared to each of the bodily condition records of the second database. This comparison provides the basis for determining any correlation between the individual's analyte values and bodily conditions maintained in the second database.

In step 6 of the method of the present invention, a determination is made, based upon the comparison of step 5, regarding any correlation between the patient analyte level set and each of the bodily condition records of the second database. The correlation between the patient analyte level set and the bodily condition records will indicate the likelihood that an individual is afflicted with the bodily condition. The comparison indicates the likelihood of bodily condition affliction by counting how many "pattern matches" exist between the analyte levels (L, N or H) of the patient analyte level set and the analyte levels for the various analytes associated with the particular bodily condition of the second database.

TABLE 7

| | DISEASE INDICATOR | | |
|---|---|---|---|
| DISEASE | # ANALYTES | # MATCHES | % MATCH |
| 1 | 5 | 0 | 0% |
| 2 | 6 | 4 | 67% |
| 3 | 5 | 2 | 40% |
| . | . | . | . |
| . | . | . | . |
| . | . | . | . |

Table 7 presents an example of the results of a comparison between the presence level of analytes associated with a particular bodily condition and the presence level of the corresponding analytes of the individual's analyte level set. The analyte presence levels (L, N or H) of the various analytes of the patient analyte level set are compared with the analyte presence levels of the analytes associated with the various diseases, for example diseases 1, 2, 3, . . . maintained in the second database and presented in Table 3. This comparison enables the system to determine the degree to which any of the diseases are indicated. By determining a percent match between the individual's analyte presence levels and the analyte presence levels for analytes associated with a particular disease, as presented in the last column of Table 7, the method of the present invention can determine the likelihood that the patient is afflicted by the particular disease. For example, as presented in Table 7, disease 2 is very likely present because 4 of 6 of the analyte levels are matched, whereas diseases 1 and 3 are not likely present because fewer of the analyte levels for these diseases are matched. Table 8 provides a more detailed example of a portion of a typical result tabulation similar to Table 7.

TABLE 8

| DISEASE | ICD-9 CODE | # OF MATCHES | # OF ANALYTES | PERCENT MATCH |
|---|---|---|---|---|
| Anterior Pituitary Hypofunction | 253.40 | 5 | 10 | 50.00% |
| Pernicious Anemia | 281.00 | 6 | 15 | 40.00% |
| Vitamin C Deficiency | 267.00 | 3 | 8 | 37.50% |
| Rheumatoid Arthritis | 714.00 | 5 | 15 | 33.33% |

TABLE 8-continued

| DISEASE | ICD-9 CODE | # OF MATCHES | # OF ANALYTES | PERCENT MATCH |
|---------|------------|--------------|---------------|---------------|
| Acute Myocardial Infarction | 410.00 | 5 | 15 | 33.33% |
| . | . | . | . | . |
| . | . | . | . | . |
| . | . | . | . | . |

In another preferred embodiment of the present invention, generating the patient analyte level set is accomplished in an alternative manner. In particular, where the manner described above for generating the patient analyte level set generated the percent status set and determined the analyte presence levels based upon the percent status set, the present manner generates a normal limit set. The normal limit set comprises analyte values that demarcate the boundaries for normal levels of the particular analyte. The normal limit set includes a high normal limit and a low normal limit.

Figure 5:
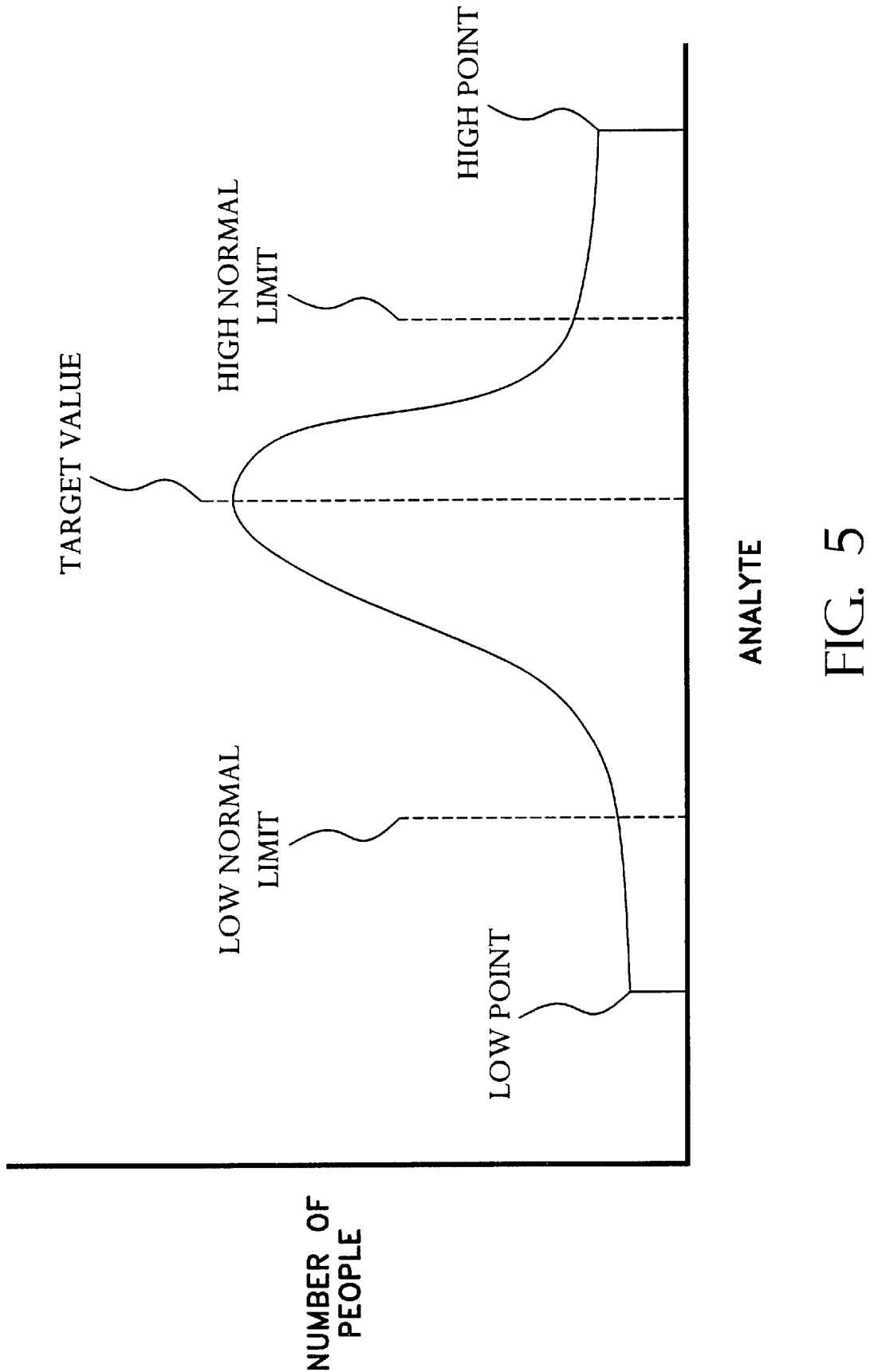
FIG. 5 is a graph illustrating another manner in which High, Low and Normal levels of an analyte are determined in conjunction with the present invention.

As illustrated in FIG. 5, a curve indicative of test results obtained from the human test group, as described above is generally a bell curve. The curve includes a lower limit, labeled "Low Point" and an upper limit, labeled "High Point." The Low Point and the High Point are determined as two standard deviations of the results of the human test group. In generating the analyte level set, the method of the present invention implementing the alternative manner of generating the patient analyte level set requires a demarcation for LOW levels, NORMAL levels, and HIGH levels. In this embodiment, the method generates a normal limit value set for each of the plurality of analytes maintained in the first database using the data information maintained in each record of the first database. The normal limit value set includes a high normal limit value (HNL) and a low normal limit (LNL) value.

The high normal limit value for each analyte is determined using the equation:

$$HNL = \text{analyte mode value} + [\text{normal percent range} * (\text{analyte high value} - \text{analyte mode value})]$$

The low normal limit value for each analyte is determined using the equation:

$$LNL = \text{analyte mode value} - [\text{normal percent range} * (\text{analyte mode value} - \text{analyte low value})]$$

The normal percent range is a constant between 0 and 1. The normal percent range is preferably between 0.25 and 0.75. The normal percent range is more preferably 0.50. For all of the analyte values of the patient analyte test result set that are less than or equal to LNL, the corresponding elements of the patient analyte level set are labeled LOW. For all of the analyte values of the patient analyte test result set that are greater than the LNL but less than the HNL, the corresponding elements of the patient analyte level set are labeled NORMAL. For all of the analyte values of the patient analyte test result set that are greater than or equal to the HNL, the corresponding elements of the patient analyte level set are labeled HIGH.

As discussed above, by generating the HNL and the LNL as a function of the analyte mode value and changing the denominator for each, the determination of the presence levels provides a more accurate indicator of the individual's analyte values relative to the most common analyte value, as shown by the mode value. This in turn provides the practitioner with a better basis for developing a course of treatment.

Therefore, the basic method presented in FIG. 2 enables a medical practitioner to input an individual's analyte values into a computerized system and have the system produce a listing of possible diseases that the individual may have based upon the variation between the individual's analyte values and the analyte values of a human test group.

Figure 6:
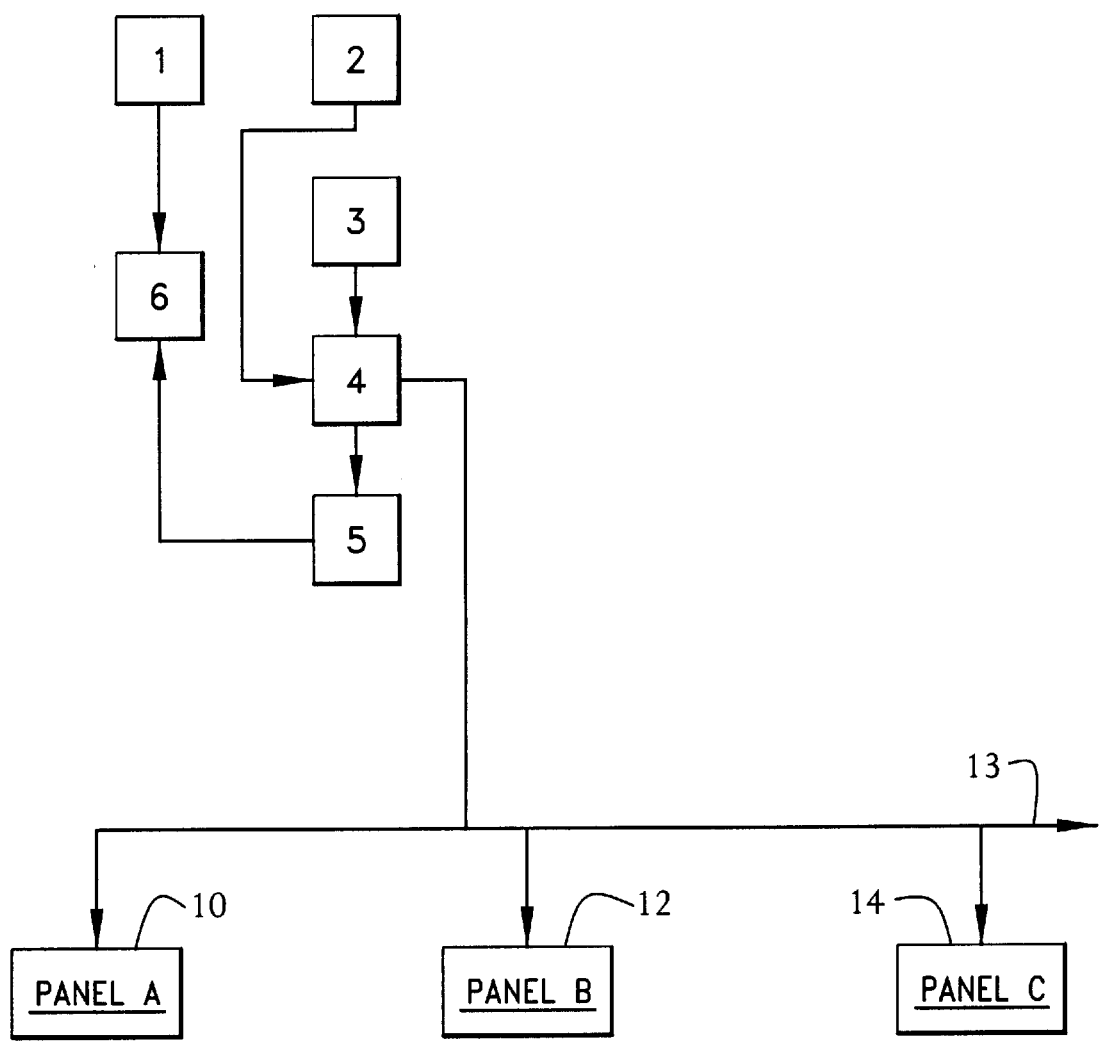
FIG. 6 is a block diagram showing the derivation of various panel status data results.

FIG. 6 illustrates a use of the percent status data, developed in step 4 of the basic method as depicted in FIG. 2 and described above, in addition to deriving the analyte level set, as described above. As described above, the analysis and diagnosis of certain bodily conditions and functions may be made based upon the analytes, denoted as 1, 2, 3 . . . 12 above. A database for a particular bodily function that includes the associated analytes and an individual's percent status for each analyte is termed a panel. Table 9 presents hypothetical data for three panels (Panel A, Panel B and Panel C) of many contemplated panels.

TABLE 9

| Panel A | | Panel B | | Panel C | |
|---------|----------|---------|----------|---------|----------|
| Analyte | % Status | Analyte | % Status | Analyte | % Status |
| 1 | 23.4 | 3 | −34. | 7 | −22. |
| 3 | −34. | 7 | −22 | 13 | 50. |
| 18 | 7.80 | 8 | −41 | 71 | −16.66 |
| 32 | −6.43 | 18 | 7.80 | | |
| | | 47 | −18.88 | | |
| | | 853 | 23.61 | | |
| Deviation | 17.91 | Deviation | 24.55 | Deviation | 29.56 |
| Skew | 2.31 | Skew | −14.08 | Skew | 3.78 |

As illustrated in FIG. 6 and presented in Table 9, panel A (see reference numeral 10) refers to a specific bodily condition or function, and information related to the panel A condition or function is obtainable from a combined analysis of analytes 1, 3, 18 and 32 (for example) wherein a percent status value from step 4 is utilized for each analyte. A mathematical data deviation (the average of percent status without regard to the sign), and a data skew (the average of the percent status wherein the sign is taken into account), is calculated for each panel data set. The deviation and skew provide a numerical framework for referencing the status of the bodily condition or function of panel A. Also presented in Table 9 and illustrated in FIG. 6 is a panel B (see reference numeral 12) that includes, for example analytes 3, 7, 8, 18, 47, and 85 wherein a percent status value from step 4 is utilized for each analyte, with a deviation and skew being reported for panel B. Also presented in Table 9 and illustrated in FIG. 6 is a panel C (see reference numeral 14) that includes, for example, analytes 7, 12 and 71 wherein a percent status value from step 4 is utilized for each analyte with a deviation and skew being reported for panel C. Current medical knowledge teaches that many such bodily functions and conditions can be represented by data panels comprising a plurality of specific analytes, and while only panels A, B and C are presented in Table 9 and illustrated in FIG. 6, arrow 13 is presented in FIG. 6 to indicate that a great number of panels may be developed. The panels presented in the tables are meant only to be exemplary and not limit the present invention.

Specific panels for bodily conditions and functions that are contemplated by the inventor include, for example, nitrogen status, electrolyte status, protein status, cardiac marker status. liver status, kidney function status, lipid status, allergy status, hematology status, leukocyte percentage differential status, blood element ratio status, leukocyte count status, acid PH analyte status, alkaline PH analyte status.

By way of specific examples to further the comprehension of the present invention, Table 10 presents the electrolyte panel, the cardiac marker panel, the kidney function status panel. and the blood elements ratio status panel of a particular individual.

TABLE 10

| ANALYTE | Result | % Status |
|---|---|---|
| ELECTORLYTE | | |
| Sodium | 139 | −10.00 |
| Potassium | 4.2 | −12.50 |
| Chloride | 105 | 50.00 |
| CO2 | 22 | −30.00 |
| Calcium | 9.7 | 19.23 |
| Phosphorus | 3.6 | −20.00 |
| Panel Status Deviation | | 23.62 |
| Panel Status Skew | | −0.54 |
| KIDNEY FUNCTION | | |
| B.U.N. | 9.0 | −41.67 |
| Phosphorus | 3.6 | −20.00 |
| Cholesterol | 181 | −17.21 |
| Creatinine | 0.5 | 0.00 |
| Uric Acid | 4.1 | 26.00 |
| Calcium | 9.7 | 19.23 |
| LDH | 414 | −31.95 |
| Total Protein | 6.5 | −30.00 |
| Albumin | 4.1 | −10.00 |
| Globulin | 2.4 | −60.00 |
| A/G Ratio | 1.7 | 23.48 |
| Panel Status Deviation | | 25.41 |
| Panel Status Skew | | −12.92 |
| RATIO'S | | |
| BUN/Creatinine | 18.00 | 13.16 |
| Sodium/Potassium | 33.10 | 9.13 |
| Calcium.Phosphorus | 2.69 | 19.72 |
| A/G Ratio | 1.71 | 23.48 |
| Anion Gap | 16.20 | 72.00 |
| Panel Status Deviation | | 27.50 |
| Panel Status Skew | | 27.50 |
| CARDIAC MARKER | | |
| Cholesterol | 181 | −17.21 |
| Triglycerides | 98.0 | 28.75 |
| SGOT | 23.0 | −5.00 |

TABLE 10-continued

| ANALYTE | Result | % Status |
|---|---|---|
| LDH | 414.0 | −31.95 |
| Panel Status Deviation | | 20.73 |
| Panel Status Skew | | −6.35 |

It is to be understood that other and further panels as identified above are within the contemplation of the inventor and will be known to those skilled in the art, and that medical research daily identifies other panels and further analytes that are suitable for usage in the various panels that may be derived utilizing the present invention.

Figure 7:
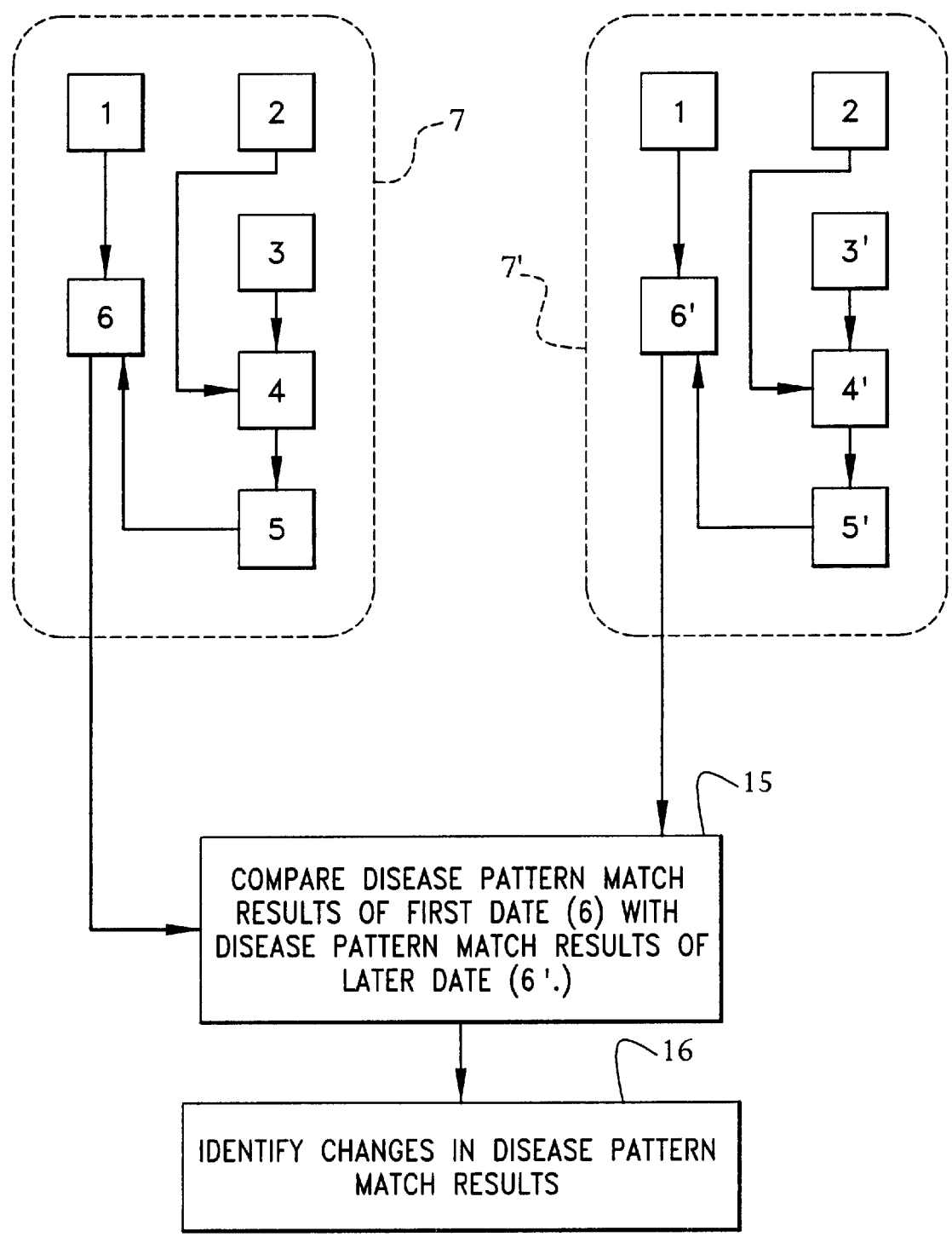
FIG. 7 is a block diagram showing the comparison of disease pattern match results of two separate dates.

The present invention contemplates the comparison of an individual's analyte values obtained through testing, as described above, on a first date with the analyte values obtained through testing the same individual on a second, later date, in order to determine changes in the individual's medical condition. FIG. 7 is a block diagram of such a comparison. Specifically, FIG. 7 illustrates a comparison of disease pattern match results. Exemplary data corresponding to FIG. 7 is presented in Table 11. As illustrated in FIG. 7 and presented in Table 11, a first set of disease pattern match data is derived from blood, urine or other fluid testing on a first date; this data is derived using element 7 of the FIG. 7. This corresponds to the method described above with reference to FIG. 2 and presented in Table 8. On a second date testing of the same individual is performed, in the same manner as performed on the first date., as represented by element 7', wherein new analyte values are obtained from the individual's test results 3'. The analyte values 3' are compared with the human test group analyte values 2 to generate new percent status data 4' for all analytes. The percent status data 4' is utilized to develop new analyte presence levels 5', and new disease pattern matches 6' as presented in Table 11. The disease pattern match data of 6 and 6' is compared 15 and changes in disease pattern matches 16 are identified (see Table 11) as a means of providing health status data related to the individual.

TABLE 11

| | | First Date | | | Second Date | | |
|---|---|---|---|---|---|---|---|
| DISEASE | ICD-9 CODE | # OF MATCHES | # OF ANALYTES | % MATCH | # OF MATCHES | % MATCH | % Change |
| Anterior Pituitary Hypofunction | 253.40 | 5 | 10 | 50.00 | 6 | 60.00 | −10.00 |
| Pernicious Anemia | 267.00 | 3 | 8 | 37.50 | 3 | 27.50 | 0 |
| Rheumatoid Arthritis | 714.00 | 5 | 15 | 33.33 | 5 | 37.50 | 0 |
| Acute Myocardial Infarction | 410.00 | 5 | 15 | 33.33 | 4 | 26.66 | +6.67 |

Figure 8:
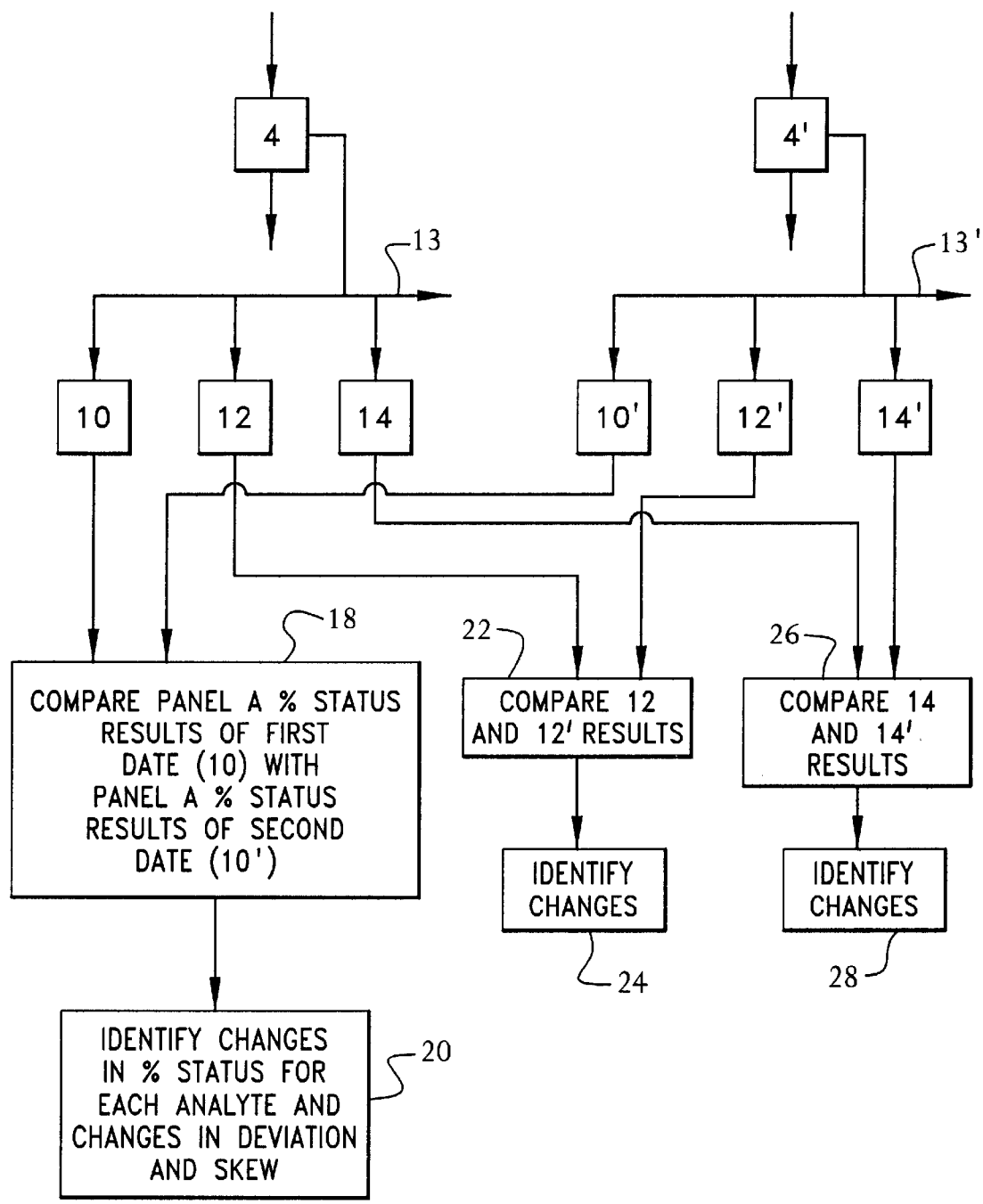
FIG. 8 is a block diagram depicting the comparison of panel status data for two separate dates.

The new percent status data developed for the second date in step 4' of FIG. 7 can be utilized to develop new panel status information for the second date in the same manner as is described above with regard to FIG. 6. Thereafter, the panel status data of the first test date can be compared with the new panel status data for the second date to provide information on the individual's medical health changes. FIG. 8 depicts such a panel status data comparison from a first date and a subsequent second date. Table 12 presents exemplary data for panels A, B and C as discussed above with regard to Table 9.

TABLE 12

| Analyte | First Date % Status | Second Date % Status | Comparison % Change |
|---|---|---|---|
| Panel A | | | |
| 1 | 23.4 | 25.0 | −1.6 |
| 3 | −34. | −28.0 | +6.0 |
| 18 | 7.80 | 7.8 | 0. |
| 32 | −6.43 | −6.43 | 0. |
| Deviation | 17.91 | | |
| Skew | −9.23 | | |
| Panel B | | | |
| 8 | −34 | −28 | +6.0 |
| 7 | −22 | −22 | 0. |
| 8 | −41 | −45 | −4.0 |
| 18 | 7.80 | 7.8 | 0. |
| 47 | −18.88 | −20.0 | −1.12 |
| 85 | 23.61 | 23.61 | 0. |
| Deviation | 24.55 | | |
| Skew | −14.08 | | |
| Panel C | | | |
| 7 | −22. | −22 | 0. |
| 13 | 50. | 42 | +8.0 |
| 71 | −16.66 | −8.4 | +8.26 |
| Deviation | 29.56 | | |
| Skew | 3.78 | | |

As illustrated in FIG. 8, percent status data from step 4 of FIG. 7 at a first date is utilized to create panel status data 10, 12 and 14 as discussed above with regard to FIG. 6 and Table 9. In an identical manner on the second date, percent status data derived in step 4' of FIG. 7 is utilized to create panel status data 10', 12' and 14' as presented in Table 12. As mentioned above, additional panels represented by arrows 13 and 13' are contemplated. A comparison 18 of panel A percent status results of the first date 10 with panel A percent status results of the second date 10' is now accomplished as is presented in Table 12. The comparison 18 is utilized to identify changes 20 in the percent status for each analyte relevant to panel A, together with changes in the deviation and skew data. In a like manner, a comparison 22 of panel B status data 12 and 12' permits the identification 24 of changes in panel B medical status. Likewise, panel C status data is compared 26 to identify changes 28 in panel C medical status.

A specific example of a panel status data comparison is presented in Table 13 wherein the panels of Table 10 are utilized, those being the electrolyte panel, the cardiac marker panel, the kidney function status panel and the blood elements ratio status panel of a particular individual. As presented in Table 13, the panel results for the first date are reproduced from Table 10 and new panel results for the second date are reported. The comparison between the first date data and the second date data also indicates whether the change in specific analytes for each panel has improved (positive) or worsened (negative), and the change in the percent status of each analyte is reported. Additionally, the mathematical deviation and skew of the first date results and the second date results are provided and the change in the deviation and skew is also reported. The panel status data change of Table 13 may be utilized by a medical practitioner to provide insight into the medical health changes that the individual has undergone during the intervening period between the first date testing and the second date testing.

TABLE 13

| ANALYTE | First Date Result | % Status | Second Date % Status | Comparison Direction | % Change |
|---|---|---|---|---|---|
| ELECTROLYTE | | | | | |
| Sodium | 139 | −10.00 | −19.09 | Negative | −9.09 |
| Potassium | 4.2 | −12.50 | −17.50 | Negative | −5.00 |
| Chloride | 105 | 50.00 | −57.69 | Negative | −7.69 |
| CO2 | 22 | −30.00 | −42.50 | Negative | −12.50 |
| Calcium | 9.7 | 19.23 | 8.12 | Positive | 11.11 |
| Phosphorus | 3.6 | −20.00 | −26.67 | Negative | −6.67 |
| Panel Status Deviation | | 23.62 | 32.30 | | −8.68 |
| Panel Status Skew | | −0.54 | −5.51 | | 4.97 |
| KIDNEY FUNCTION | | | | | |
| B.U.N. | 9.0 | −41.67 | −57.05 | Negative | −15.38 |
| Phosphorus | 3.6 | −20.00 | −26.67 | Negative | −6.67 |
| Cholesterol | 181 | −17.21 | −4.64 | Positive | 12.57 |
| Creatinine | 0.5 | 0.00 | −14.29 | Negative | −14.29 |
| Uric Acid | 4.1 | 26.00 | 28.00 | Negative | −2.00 |
| Calcium | 9.7 | 19.23 | 8.12 | Positive | 11.11 |
| LDH | 414. | −31.95 | −45.90 | Negative | −13.95 |
| Total Protein | 6.5 | −30.00 | −38.00 | Negative | −8.00 |
| Albumin | 4.1 | −10.00 | 12.22 | Positive | 22.22 |
| Globulin | 2.4 | −60.00 | −50.48 | Positive | 9.52 |
| A/G Ratio | 1.7 | 23.48 | −4.61 | Positive | 28.09 |
| Panel Status Deviation | | 25.41 | 12.34 | | 13.07 |
| Panel Status Skew | | −12.92 | −10.81 | | 2.11 |
| RATIO'S | | | | | |
| BUN/Creatinine | 18.00 | 3.16 | 1.41 | Positive | 1.75 |
| Sodium/ Potassium | 33.10 | 9.13 | 11.67 | Negative | −2.54 |
| Calcium/ Phosphorus | 2.69 | 19.72 | 24.18 | Negative | −4.46 |
| A/G Ratio | 1.71 | 23.48 | −4.61 | Positive | 28.09 |
| Anion Gap | 16.20 | 72.00 | 71.00 | Positive | 1.00 |
| Panel Status Deviation | | 27.50 | 24.57 | | 2.93 |
| Panel Status Skew | | 27.50 | 22.43 | | 4.77 |
| CARDIAC MARKER | | | | | |
| Cholesterol | 181 | −17.21 | −29.78 | Positive | 12.57 |
| Triglycerides | 98.0 | 28.75 | 29.25 | Negative | −0.50 |
| SGOT | 23.0 | −5.00 | −7.38 | Negative | −2.38 |
| LDH | 414.0 | −31.95 | −45.90 | Negative | −13.95 |
| Panel Status Deviation | | 20.73 | 13.38 | | 7.35 |
| Panel Status Skew | | −6.35 | −7.42 | | −1.07 |

A further feature of the present invention is the generation of a report indicating the known effects of various drugs on analyte levels. As illustrated in step of FIG. 9, and presented as an example in Table 14, a third database is created and stored on the storage medium. The third database includes drug records that correlate the effects of known drugs upon the levels of each of the various analytes. Thus, as presented in Table 14, for each analyte 1, 2, 3 . . . known drugs are cataloged that can cause or increase an analyte value that has already been determined to be a HIGH analyte presence level (H) and that can cause or decrease an analyte value that has already been determined to be a LOW analyte presence level (L). The effects of the various drugs on the various analyte levels are well known in medical research and new drugs, and the corresponding effects thereof on various analytes are developed in medical research on a daily basis.

TABLE 14

| | DRUG (a, b, c . . .) CAUSE OR AGGRAVATE | |
|---|---|---|
| ANALYTE | HIGH (H) | LOW (L) |
| 1 | a, b, d, f, h | l, m, p |
| 2 | a, c, e, j, l | b, d, o, p |
| 3 | b, c, f, g | d, j, k, l, m |
| 4 | a, d, g, h | b, f, k |
| 5 | a, c, f, h, k, l | b, d, e, o, p |
| 6 | e, h, k, m | a, d, l, r, t |
| . | . | . |
| . | . | . |
| . | . | . |

Figure 9:
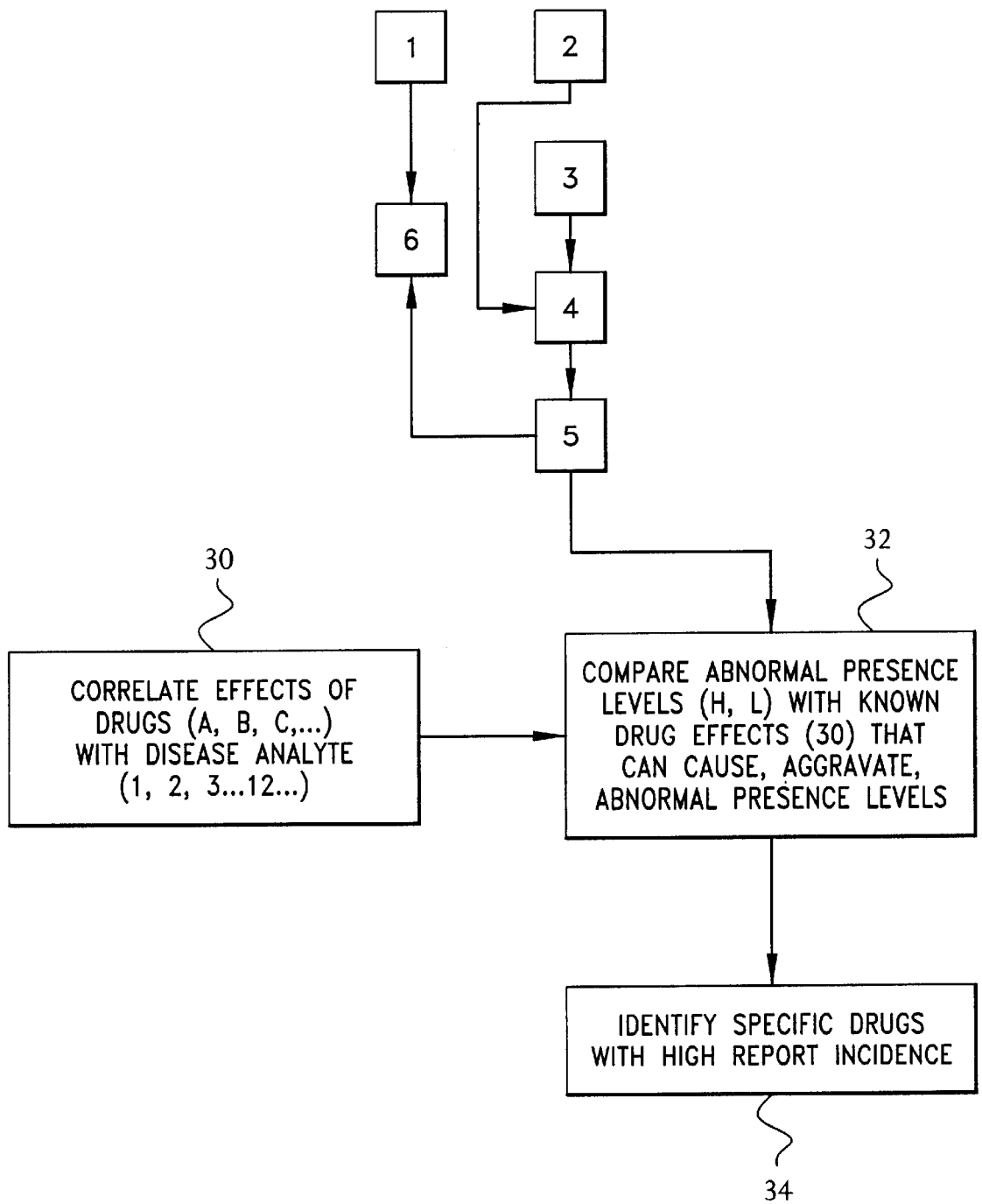
FIG. 9 is a block diagram showing the incorporation of known drug effect data with analyte status levels o the present invention.

As illustrated in FIG. 9, the next step 32 in this analysis is to compare the abnormal presence levels, both HIGH (H) and LOW (L), determined in step 4 of the basic method of the present invention, with the drug effects data presented in Table 14. By way of example, Table 6 shows that a specific individual's test results indicated that analytes 1 and 2 showed a NORMAL presence level, analyte 3 had a LOW presence level, analyte 4 had a HIGH presence level, and analytes 5 and 6 had LOW presence levels.

Table 15 presents the abnormal analytes 3, 4, 5 and 6, their HIGH or LOW presence level, and identifies the specific drugs from Table 14 that cause HIGH or LOW presence level of the analyte, as described above.

TABLE 15

| ANALYTE | ABNORMAL PRESENCE LEVEL | DRUG CAUSE OR AGGRAVATE |
|---|---|---|
| 3 | L | d, j, k, l, m |
| 4 | H | a, d, g, h |
| 5 | L | b, d, e, o, p |
| 6 | L | a, d, l, r, t |
| . | . | . |
| . | . | . |
| . | . | . |

HIGH INCIDENCE DRUG = d (CONTRAINDICATED)

After comparing the analyte presence levels and the drugs related to the particular analyte, as presented in Tables 14 and 15, the incidence of the various drugs presented in Table 15 is determined, as set indicated by step 34 of FIG. 9. Specifically, it can be seen in Table 15 that drug "d" is identified as a drug that can cause or aggravate each of the abnormal presence levels of each of the analytes presented in Table 15. The analytical result of this analysis is the conclusion that drug "d" is contraindicated for this individual.

To further enhance the understanding of the present invention, Table 16 presents known drug effect medical research data for a few specific analyte conditions. Specifically, for the analyte chloride level in blood testing, where the chloride level is high (percent status is greater than 25), some known drugs that can cause or aggravate this condition are listed; aspirin is one of these drugs. For the total iron level analyte, which is low (percent status is less than −25), some known drugs that can cause or aggravate this reduced level are provided. For the basophils analyte level, which is low (percent status is less than −25), a drug that can cause or aggravate this low level is procainamide. For the white blood count (WBC) level analyte having a low level (percent status is less than −25), drugs that can cause or aggravate this reduced level are listed, and it is specifi-cally noted that aspirin is one of the drugs. For the glucose level analyte having a low level (percent status is less than −25), drugs which cause or aggravate the low level are identified, and it is specifically noted that aspirin is one such drug. The last analyte presented in Table 16 (it being understood that as many analytes as are identified in test results as having an high or low levels would be included in Table 16) is total protein having a low level (percent status is less than −25), and some of the various drugs that can cause or aggravate the reduced level are identified, specifically identifying aspirin as one of the drugs.

TABLE 16

| ANALYTE | ABNORMAL PRESENCE LEVEL | DRUG CAUSE OR AGGRAVATE CONDITION |
|---|---|---|
| Chloride | L | Acetazolamide, Asprin, Lithium, Boric Acid . . . |
| Total iron | L | ACTH, Oxalate, Fluorides . . . |
| Basophils | L | Procainamide . . . |
| WBC | L | Aspirin, Busulfan, Mepazine . . . |
| Glucose | L | Aspirin, Ethanol, Insulin |
| Total Protein | L | Aspirin, Arginine, Rifampin . . . |

An analysis of the data presented in Table 16 shows that the drug aspirin is identified as a drug that can cause or aggravate four of the six abnormal presence levels of the analytes set forth therein; thus aspirin is a contraindicated drug for the individual whose test results are provided in Table 16.

Figure 10:
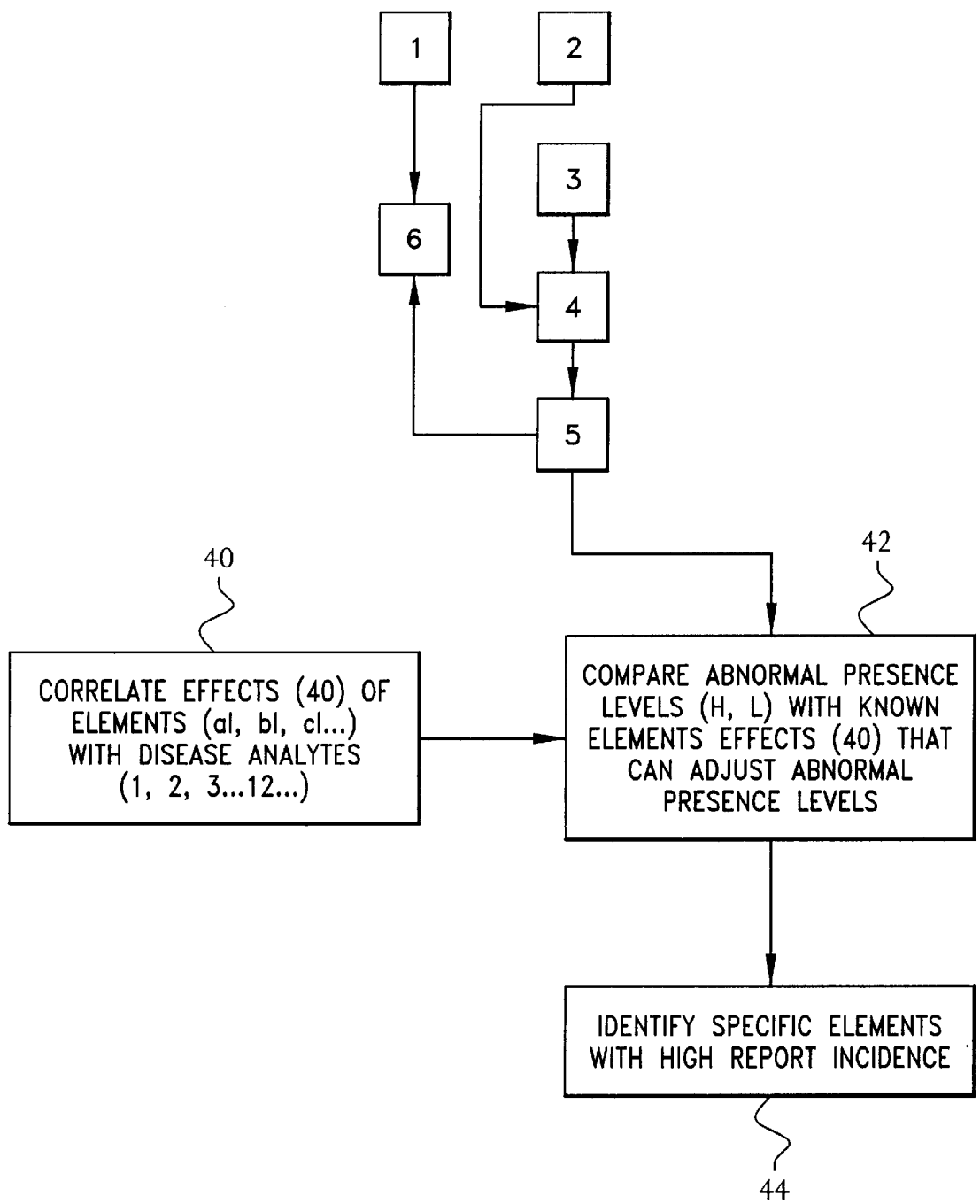
FIG. 10 is a block diagram showing the utilization of known effects of nutritional-biochemical elements with analyte levels.

It is therefore to be generally understood that the present invention includes a method as shown in FIG. 9 to identify specific drugs that are contraindicated for an individual based upon the high or low levels of specific analytes in the individual's blood/fluid test analysis results. This output data of contraindicated drugs is obtained utilizing a database 30 that correlates high and low analyte levels with known drug effects from known medical research, and the specific analytes identified in step 5 test results as having high or low levels pursuant to the analytical methods of the present invention. Another feature of the present invention is the incorporation of the known positive effects of various pharmacological agents upon test results for various analyte levels. As illustrated in FIG. 10, and the example presented in Table 17, a pharmacological agents database is created and stored 40 in the storage medium. The agents database includes agent records that correlate the effects of known pharmacological agents (al, bl, cl, . . . ) upon the levels for each of the various analytes. Table 17 is similar to Table 14 with the significant difference that the effect of the pharmacological agents is to improve the abnormal presence level of various analytes.

TABLE 17

| | PHARMACOLOGICAL AGENT (a1, b1, c1 . . .) EFFECT | |
|---|---|---|
| ANALYTE | INCREASE (I) | DECREASE (D) |
| 1 | b1, d1, f1, h1 | c1, k1, r1 |
| 2 | a1, g1, I1 | c1, I1, s1, t1 |
| 3 | d1, g1, h1, k1 | b1, c1, m1 |
| 4 | a1, k1, m1 | c1, d1, I1 |
| 5 | c1, k1, r1, s1 | a1, f1, g1, m1, p1 |
| 6 | a1, c1, n1, t1, v1 | d1, h1, k1, m1, s1 |
| . | . | . |
| . | . | . |
| . | . | . |

Thus, as presented in Table 17, for each analyte 1, 2, 3 . . . 12 . . . known agents are cataloged that can normalize the level of a particular analyte; that is, to reduce an high level or to raise a low level. The effects or the various pharmacological agents on the various analyte levels are well known in medical research. New agents, and the corresponding effects thereof on various analytes are developed in medical research on a daily basis.

As illustrated in FIG. 10, the next step 42 in this analysis is to compare the abnormal presence levels, both high (H) and low (L), determined in step 4 of the basic method of the present invention with the pharmacological agent data of Table 17. By way of example, it is presented above in Table 6 that a specific individual's test results showed that analytes 1 and 2 showed a normal presence level, analyte 3 had a low presence level, analyte 4 had an high presence level, analytes 5 and 6 had low presence levels. Table 18 presents the abnormal analytes 3, 4, 5 and 6 with their high or low presence level, and identifies the specific pharmacological agents from Table 17 that can have a positive effect on the abnormal presence level indicated.

TABLE 18

| ANALYTE | ABNORMAL PRESENCE LEVEL | PHARMACOLOGY AGENT EFFECT |
|---|---|---|
| 3 | L | b1, c1, m1 |
| 4 | H | a1, k1, m1 |
| 5 | L | a1, f1, g1, m1, p1 |
| 6 | L | d1, h1, k1, m1, s1 |
| . | . | . |
| . | . | . |
| . | . | . |

HIGH INCIDENCE AGENT = m1 (INDICATED)

Thereafter, in step 44 of FIG. 10, the incidence of the various pharmacological agents presented in Table 18 is determined. Specifically, it is seen in Table 18 that pharmacological agent "m1" is identified as an agent that can have a positive effect on each of the abnormal presence levels of each of the analytes. The analytical result of this analysis is the conclusion that pharmacological agent "m1" is positively indicated for this individual.

Figure 11:
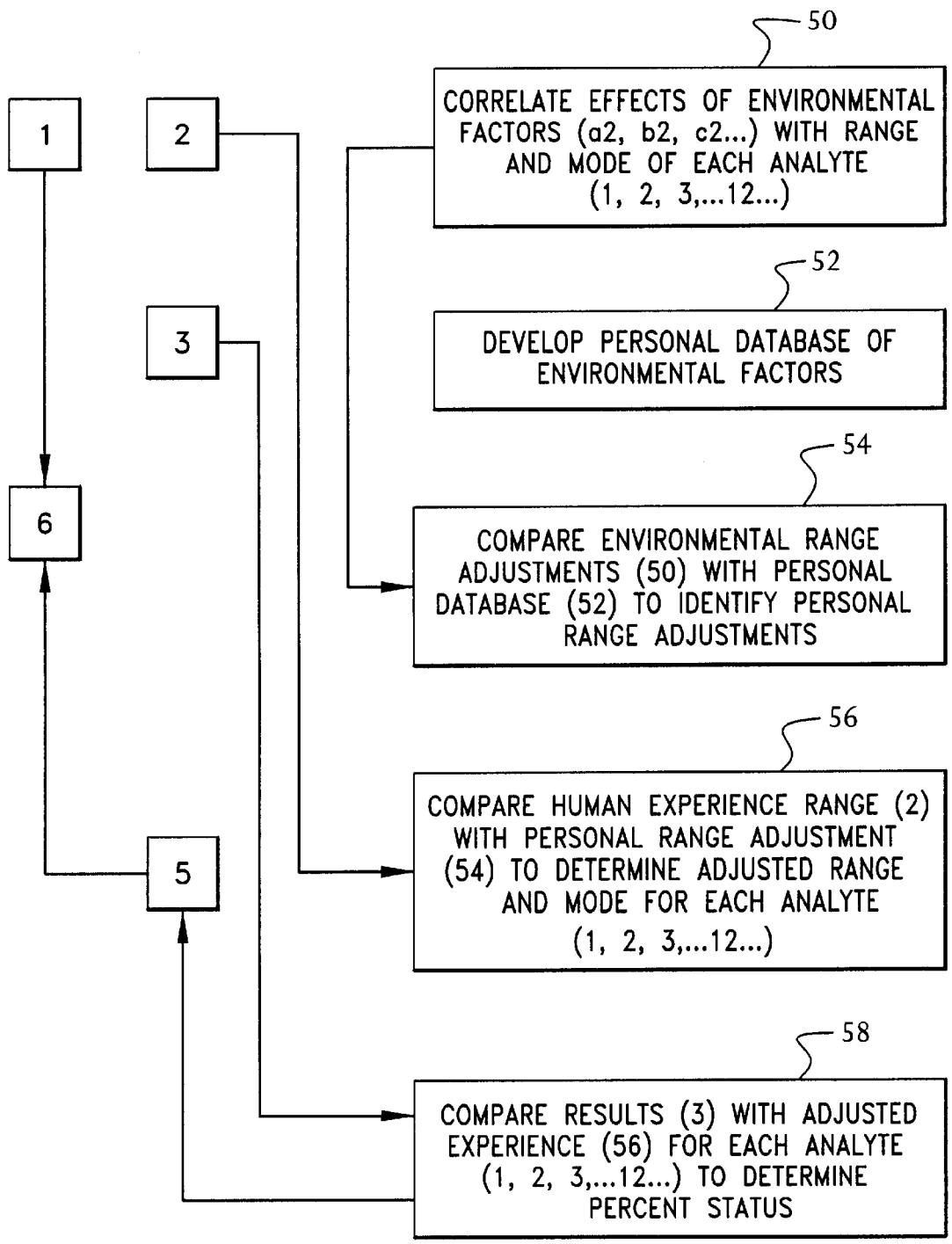
FIG. 11 is a block diagram showing the utilization of the known effects of various personal and/or environmental factors with the diagnostic system at the present invention.

It is well known in medical research that various environmental/personal factors can affect the analyte levels of an individual, or segments of the population generally. For example, such factors as age, sex, race, pregnancy, residence location, previous or current diseases, previous or current drug usage, etc., can all affect the various analyte levels. That is, a particular analyte level might be normal for a ten year old male and abnormal (high or low) for a 65 year old female. FIG. 11 illustrates the analytical steps of the present invention that incorporate the various environmental/personal factors.

As illustrated in FIG. 11, a first step 50 in this portion of the analysis method of this invention is to create a database that correlates the effects of various environmental/personal factors (a2, b2, c2, . . . ) with the range and mean of each analyte (1, 2, 3 . . . 12 . . . ), and Table 19 presents an example of such a database showing the effects of various factors, such as sex, pregnancy, altitude of residence and prior disease on the range (low and high) of various analytes, showing that some analyte ranges are affected by some of the factors whereas other analyte ranges are not.

TABLE 19

| | | | factors (a2, b2, c2 . . . ) | | | | | | |
|---|---|---|---|---|---|---|---|---|---|
| ANA- | RANGE | | SEX | | PREG-NANCY | | ALTI-TUDE | | PRIOR DISEASE |
| LYTE | LOW | HIGH | L | H | L | H | L | H | L | H |
| 1 | .9 | 2 | .6 | 1.5 | 1.2 | 4 | .4 | 1.0 | — | — |
| 2 | 3.5 | 5 | — | — | 5 | 10 | — | — | — | — |
| 3 | 60 | 415 | 80 | 600 | 30 | 300 | — | — | 30 | 400 |
| 4 | 4 | 14 | 5 | 18 | — | — | — | — | — | — |
| 5 | 0 | 3 | 0 | 2 | 0 | 6 | — | — | 0 | 6 |

The initial range results from Table 3 are presented for illustrative purposes.

Thereafter, as illustrated in FIG. 11, an individual database of environmental/personal factors is created 52. Such a database is presented by way of example in Table 20.

TABLE 20

INDIVIDUAL ENVIRONMENTAL/PERSONAL FACTORS
Age-45,    Sex-M,    Residence-High Altitude, Prior Disease-hypothyroid, current drugs-thyroxin, aspirin.

The data presented Table 20 is obtained through a detailed medical background investigation and questionnaire responses of the individual.

In the next step 54 of this analysis, the environmental factor database 50 and the individual database of environmental factors 52 are compared 54 to identify the range adjustments of the specific analytes that require modification based upon the particular individual's environmental/personal factors. Such a comparison 54 is presented in Table 21 wherein it is seen that no adjustment to the normal levels (low and high) for analytes 2 and 4 is required, whereas adjustments for analyte levels 1, 3 and 5 are required due to the existence and effect of particular environmental/personal factors (altitude and prior disease) for this individual.

TABLE 21

| | INDIVIDUAL FACTORS | | | |
|---|---|---|---|---|
| | ALTITUDE | | PRIOR DISEASE | |
| ANALYTE | L | H | L | H |
| 1 | .4 | 1.0 | — | — |
| 2 | — | — | — | — |
| 3 | — | — | 30 | 400 |
| 4 | — | — | — | — |
| 5 | — | — | 0 | 6 |
| . . . | . . . | . . . | . . . | . . . |

The next step 56 in this analysis is to compare the human experience range data from the database of step 2 (see Tables 3 and 4) to create an adjusted range and mean for each analyte 1, 2, 3 . . . 12 . . . ). The result of this step 56 is the creation of a complete analyte database, similar to Table 3, wherein the individual factors are incorporated therewithin. Table 22 presents such a combined database.

TABLE 22

| ANALYTE | LOW | HIGH | MODE |
| --- | --- | --- | --- |
| 1 | 25 | 150 | 90 |
| 2 | 5 | 26 | 14 |
| 3 | 8.5 | 10.8 | 9.6 |
| 4 | 96 | 109 | 103 |
| 5 | 1.9 | 3.5 | 2.6 |
| . | . | . | . |
| . | . | . | . |
| . | . | . | . |

The next step 58 in the analysis is to compare the blood/fluid test results of the individual (as derived in step 3 of the basic method of the present invention) with the adjusted analyte database (see Table 22 from step 56). This step 58 is substantially identical to step 4 of the basic analysis, with the single difference being the utilization of the adjusted analyte levels from step 56 (as shown in Table 22) in place of the database created in step 1 of the basic method. The result of this step 58 is the creation of the percent status level for each analyte. This percent status level is derived utilizing the equation set forth in step 4 above:

if the individual's analyte value is greater than the analyte mode value than,

% Status=50*(patient test result analyte value−analyte mode value)/(analyte high value−analyte mode value)

if the individual's analyte value is less than the analyte mode value than,

% Status=50*(patient test result analyte value−analyte mode value)/(analyte mode value−analyte low value)

As discussed above with regard to the basic method, the percent status level is a mathematical value which expresses a comparison of the individuals test results for a specific analyte with the database of expected values and ranges for that analyte. Thereafter, the percent status data from step 58 is utilized to determine the analyte presence levels (H, N, or L) in the identical matter described above in step 4 with regard to the basic method. The analyte presence level data may then be utilized in any and all of the analytical methods described above.

Figure 12:
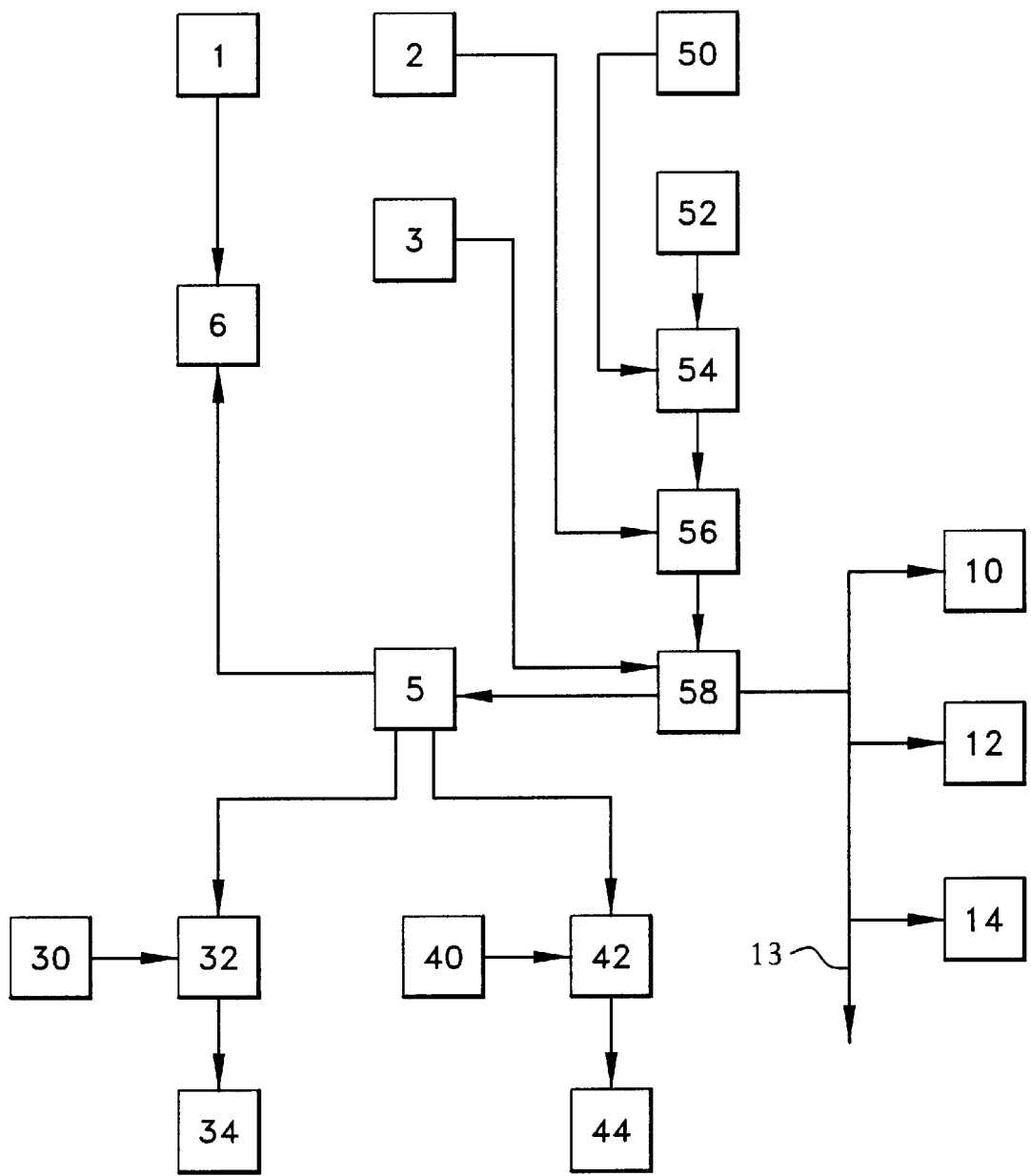
FIG. 12 is a block diagram showing the incorporation of the various analytical methods of FIGS. 6, 9, 10 and 11 with the basic diagnostic method of FIG. 2.

A comprehensive schematic diagram of the test method of the present invention is illustrated in FIG. 12. As illustrated therein and discussed above, the result of step 58 is the development of percent status levels of all of the analytes based upon the individual's blood/fluid rest results (step 3) and individualized analyte ranges (step 56). The percent status levels from step 58 may then be utilized in creating panels 10, 12, 14. Additionally, the percent status levels from step 58 are utilized in step 4 to identify presence levels of the analytes (low, normal and high). The presence levels may then be utilized in a disease pattern match analysis in step 6, and/or they may be utilized in a drug effect analysis in steps 30, 32 and 34, and/or a pharmacological agent analysis in steps 40, 42 and 44, all as have been discussed above.

Figure 13:
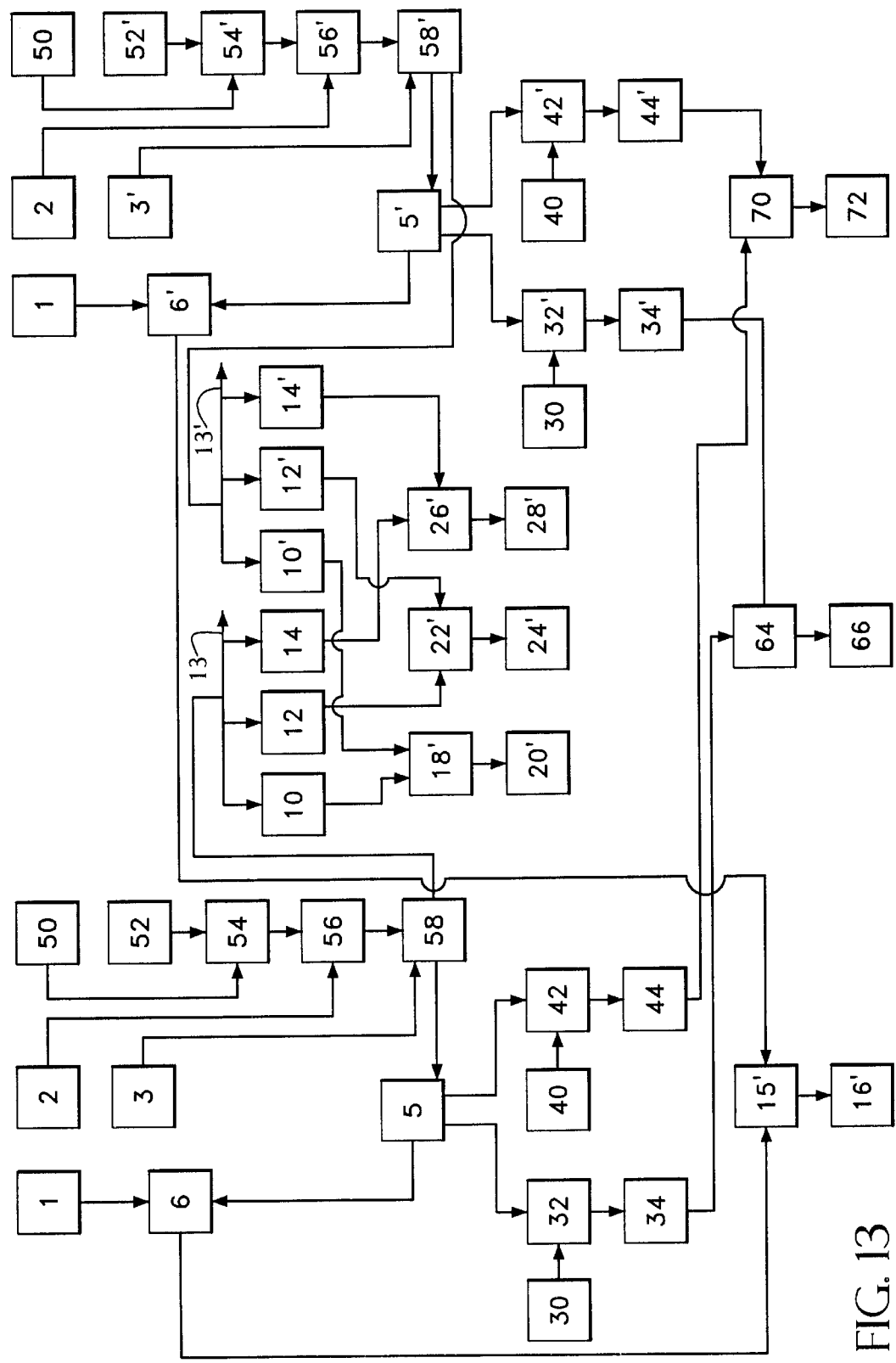
FIG. 13 is a block diagram showing the analytical method depicted in FIG. 9 utilizing individual test data from two separate dates and including data comparisons from those dates, including those shown in FIGS. 7 and 8.

FIG. 13 is a block diagram illustrating the analysis method of FIG. 12 utilized on two different dates (a first date and a second date) to develop comparative medical results. The development of such comparative results is discussed above with regard to FIGS. 7 and 8. It is therefore to be understood that on a first date a full analysis is conducted to provide disease pattern match data 6, panel data 10, 12, 14, drug interaction data 34 and pharmacological agent output data 44. Thereafter, on the second date further disease pattern match data 6", panel data 10", 12" and 14", drug interaction data 34" and pharmacological agent output data 44" are created. The corresponding data from the two dates (the first date and the second date) may then be compared to provide comparative medical data reflective of the individual's medical health changes. Thus, the disease pattern match data 6 and 6" may be compared 15" to provide results indicative of changed disease pattern matches.

Similarly, panel data 10 and 10", 12 and 12", 14 and 14" may be compared, 18", 22" and 26" respectively, to yield medical results 20", 24" and 28" respectively indicating changes in panel results. Additionally, drug interaction results 34 and 34B may be compared 64 to provide data regarding changes in drug interactions that have occurred in the intervening time period between the first date and date B. Furthermore, the pharmacological agent data 44 and 44B may be compared 70 to yield data indicative of changes in pharmacological results during the time period.

It is therefore to be understood that the medical diagnostic analysis method of the present invention provides a comprehensive means for the utilization of individual blood/fluid test results, which may be combined with environmental/personal factors related to a specific individual to yield significant medical data that is personalized and relevant to the individuals medical health.

In addition, the present invention provides a method for identifying supportive nutrients and vitamins for the individual based upon the generated analyte level set. Another database is created and stored in the storage medium. This database maintains a data information regarding a plurality of vitamins and nutrients. The database includes a vitamin/nutrient record for each of the plurality of vitamins and nutrients. Each particular vitamin/nutrient record also includes a set of analytes upon which the particular vitamin or nutrient has a supportive effect. By supportive effect, it is meant that the vitamin or nutrient drives a particular analyte towards the normal range. For instance, if an individual's particular analyte value has been determined to fall within the HIGH range, than the vitamin or nutrient that has that analyte in its database record will drive the analyte level lower and towards the NORMAL range. To this end, once the individual's analyte level set has been generated, it can be compared to the vitamin/nutrient database. This comparison will provide a group of nutrients and/or vitamins that can be prescribed to the individual to drive the analyte levels towards the normal. Table 23 is an example of a chart indicating recommended vitamins and/or nutrients for a vitamin/nutrient database for HIGH, LOW and NORMAL analyte levels. Table 23 illustrates an example of a vitamin/nutrient database. The database includes a plurality of vitamins and nutrients, for example Acetic Acid. The vitamin or nutrient has analytes associated with it correlated with an analyte level. The database indicates the particular vitamins or nutrients that are suggested to drive an out of normal range analyte level towards the normal range. As shown, Acetic Acid is suggested for a HIGH and/or NORMAL calcium level and a HIGH sodium level.

The present invention also provides for method for identifying vitamins and/or nutrients for an individual whose analyte values suggest a minor imbalance. By minor imbalance it is meant that the percent status values fall between 12.5 and 25 or between −12.5 and −25. To this end, the percent status values may be input to the CPU and compared to the vitamin/nutrient database to determine the vitamins and/or nutrients that would drive the individual's analyte values towards the mode value.

TABLE 23

| Low | Normal | High |
|---|---|---|
| | Abalone | |
| | Adult: Child: | |
| Cholesterol | Cholesterol | Eosinophils |
| CO2 | CO2 | |
| GGT | Eosinophils | |
| Potassium | GGT | |
| Sodium | Potassium | |
| | Sodium | |

Acetic Acid
Adult: BID 1 tsp. Mix in 8 oz distilled water
Child: QD ½ tsp. Mix in 8 oz distilled H2O
ACETIC ACID
Acetic acid (white vinegar), having an affinity for sodium, is supportive in lowering elevated sodium levels by displacing Na from NaCl and forming sodium acetate which is then cleared through the kidneys.

| | Calcium | Calcium |
|---|---|---|
| | | Sodium |

Acetyl Carnitine
Adult: BID 250 mg    Child: QD 125 mg
ACETYL-L-CARNITINE
An amino acid essential for transport of fatty acids through mitochondria for beta oxidation, subsequently as an energy carrier, metabolic facilitator and membrane protectant.

| W.B.C. | | Cholesterol |
|---|---|---|
| | | Triglycerides |
| | | W.B.C. |
| | Acorn Squash | |
| | Adult: Child: | |
| Calcium | Calcium | |
| GGT | GGT | |
| | Adenosylcobalamin | |

Adult: BID 1000 mg    Child: QD 1000 mcg

| Phytanic | | Lignoceric C24:0 |
|---|---|---|
| Pristanic | | Phytanic |
| | | Pristanic |
| | Advera | |

Adult: BID 8 oz+    Child: BID 4 oz+
ADVERA
Supplementation of enteral formulas applicable in metabolic signs of catabolism and low nutrient density.

| B.U.N. | | |
|---|---|---|
| Protein, Total | | |
| Uric Acid | | |

What is claimed is:

1. A medical diagnostic method utilizing a central processing unit and a storage medium coupled to the central processing unit, comprising the steps of:

storing a first database for maintaining analyte data information for a plurality of analytes in the storage medium, the first database including an analyte record for each one of the plurality of analytes, each analyte record including an analyte low value, an analyte high value and an analyte mode value indicative of a statistical analysis of analyte values obtained from testing a human test group;

storing a second database for maintaining bodily condition data information for a plurality of bodily conditions in the storage medium, the second database including a bodily condition record for each one of the plurality of bodily conditions. each bodily condition record including a set of analytes associated with the particular bodily condition, each analyte of the analyte set having an analyte level indicative of the particular bodily condition;

inputting a patient analyte test result set into the central processing unit, the patient analyte test result set including an analyte value for at least one of the plurality of analytes;

generating a patient analyte level set from the patient analyte test result set and the analyte data information of the first database;

comparing the patient analyte level set to each of the plurality of bodily condition records; and determining a correlation between the patient analyte level set and each of the bodily condition records.

2. A medical diagnostic method as set forth in claim 1, wherein the step of generating the patient analyte level set comprises the step of generating a patient percent status set, the patient percent status set comprising a value for each of the plurality of analytes in the patient analyte test result set.

3. A medical diagnostic method as set forth in claim 2, wherein the step of generating the patient percent status set comprises calculating a percent status value for each element of the patient percent status set using the following:

if the patient analyte test result value is greater than the analyte mode value then percent status=50*(patient analyte test result value−analyte mode value)/(analyte high value−analyte mode value)

and, if the patient analyte test result value is less than the analyte mode value then percent status=50*(patient analyte test result value−analyte mode value)/(analyte mode value−analyte low value).

4. A medical diagnostic method as set forth in claim 3, wherein the step of generating the patient analyte level set further comprises the step of comparing the patient percent status set to a preselected high status value and a preselected low status value.

5. A medical diagnostic method as set forth in claim 4, wherein the preselected high status value is 25 and the preselected low status value is −25.

6. A medical diagnostic method as set forth in claim 5, wherein the step of generating the patient analyte level set further comprises the step of labeling the analyte level for each element of the patient analyte level set LOW if corresponding elements of the patient percent status set are less than or equal to −25, labeling the analyte level for each element of the patient analyte level set NORMAL if corresponding elements of the patient percent status set are greater than −25 and less than 25, and labeling the analyte level for each element of the patient analyte level set HIGH if corresponding elements of the patient percent status set are greater than or equal to 25.

7. A medical diagnostic method as set forth in claim 1, wherein the step of generating the patient analyte level set comprises the step of generating a normal limit value set for each of the plurality of analytes.

8. A medical diagnostic method as set forth in claim 7, wherein the normal limit value set includes a high normal limit value and a low normal limit value.

9. A medical diagnostic method as set forth in claim 8, wherein the high normal limit value is given by the equation high normal limit value=analyte mode value+(normal percent range)*(analyte high value−analyte mode value)

and the low normal limit value is given by the equation, low normal limit value=analyte mode value−(normal percent range)*(analyte mode value−analyte low value), wherein the normal percent range being a preselected value between 0 and 1.

10. A medical diagnostic method as set forth in claim 9, wherein the step of generating the patient analyte level set further comprises the step of labeling the elements of the patient analyte level set LOW if the corresponding elements of the patient analyte test result set are less than the low normal limit value, labeling the elements of the patient analyte level set NORMAL if the corresponding elements of the patient analyte test result set are greater than the low normal limit value and less than the high normal limit value, and labeling the elements of the patient analyte level set HIGH if the corresponding elements of the patient analyte test result set are greater than the high normal limit value.

11. A medical diagnostic method as set forth in claim 1, wherein the plurality of analytes comprises red cell membrane fatty acids.

12. A medical diagnostic method as set forth in claim 1, wherein the plurality of analytes comprises blood analytes.

13. A method for identifying supportive vitamins/nutrients utilizing a central processing unit and a storage medium coupled to the central processing unit, comprising the steps of:

storing a first database for maintaining analyte data information for a plurality of analytes in the storage medium, the first database including an analyte record for each one of the plurality of analytes, each analyte record including an analyte low value, an analyte high value and an analyte mode value indicative of a statistical analysis of analyte values obtained from testing a human test group;

storing a second database for maintaining vitamin/nutrient information for a plurality of vitamins/nutrients in the storage medium, the second database including a vitamin/nutrient record for each one of the plurality of vitamins/nutrients, each vitamin/nutrient record including a set of analytes associated with the particular vitamin/nutrient and an effect the particular vitamin/nutrient has on the associated analytes;

inputting a patient analyte test result set into the central processing unit, the patient analyte test result set including an analyte value for at least one of the plurality of analytes;

generating a patient analyte level set from the patient analyte test result set and the analyte data information of the first database, the patient analyte level set including a patient analyte level for each analyte in the analyte test result set;

comparing the patient analyte level set to each of the plurality of vitamin/nutrient records; and determining a group of vitamins/nutrients that has supportive effects on the patient analyte levels.

14. A method for identifying supportive vitamins and nutrients as set forth in claim 13, wherein the step of generating the patient analyte level set comprises the step of generating a patient percent status set, the patient percent status set comprising a value for each of the plurality of analytes in the patient analyte test result set.

15. A method for identifying supportive vitamins and nutrients as set forth in claim 14, wherein the step of generating the patient percent status set comprises calculating a percent status value for each element of the patient percent status set using the following:

if the patient analyte test result value is greater than the analyte mode value then percent status=50*(patient analyte test result value−analyte mode value)/(analyte high value−analyte mode value)

and, if the patient analyte test result value is less than the analyte mode value then percent status=50*(patient analyte test result value−analyte mode value)/(analyte mode value−analyte low value).

16. A method for identifying supportive vitamins and nutrients as set forth in claim 15, wherein the step of generating the patient analyte level set further comprises the step of comparing the patient percent status set to a preselected high status value and a preselected low status value.

17. A method for identifying supportive vitamins and nutrients as set forth in claim 16, wherein the preselected high status value is 25 and the preselected low status value is −25.

18. A method for identifying supportive vitamins and nutrients as set forth in claim 17, wherein the step of generating the patient analyte level set further comprises the if step of labeling the analyte level for each element of the patient analyte level set LOW if corresponding elements of the patient percent status set are less than or equal to −25, labeling the analyte level for each element of the patient analyte level set NORMAL if corresponding elements of the patient percent status set are greater than −25 and less than 25, and labeling the analyte level for each element of the patient analyte level set HIGH if corresponding elements of the patient percent status set are greater than or equal to 25.

19. A method for identifying supportive vitamins and nutrients as set forth in claim 18, wherein the step of generating the patient analyte level set comprises the step of generating a normal limit value set for each of the plurality of analytes.

20. A method for identifying supportive vitamins and nutrients as set forth in claim 19, wherein the normal limit value set includes a high normal limit value and a low normal limit value.

21. A method for identifying supportive vitamins and nutrients as set forth in claim 20, wherein the high normal limit value is given by the equation high normal limit value=analyte mode value+(normal percent range)*(analyte high value−analyte mode value)

and the low normal limit value is given by the equation, low normal limit value=analyte mode value−(normal percent range)*(analyte mode value−analyte low value), wherein the normal percent range being a preselected value between 0 and 1.

22. A method for identifying supportive vitamins and nutrients as set forth in claim 21, wherein the step of generating the patient analyte level set further comprises the step of labeling the elements of the patient analyte level set LOW if the corresponding elements of the patient analyte test result set are less than the low normal limit value, labeling the elements of the patient analyte level set NORMAL if the corresponding elements of the patient analyte test result set are greater than the low normal limit value and less than the high normal limit value, and labeling the elements of the patient analyte level set HIGH if the corresponding elements of the patient analyte test result set are greater than the high normal limit value.

23. A method for identifying supportive vitamins and nutrients as set forth in claim 13, further comprising the step of gathering the vitamin/nutrient information for a plurality of vitamins/nutrients and generating the second database.

24. A method for identifying supportive vitamins and nutrients as set forth in claim 13, wherein the plurality of analytes comprises red cell membrane fatty acids.

25. A method for identifying supportive vitamins and nutrients as set forth in claim 13, wherein the plurality of analytes comprises blood analytes.

26. A computer program embodied on a computer-readable medium for analyzing analyte levels of an individual, comprising:
   an analysis source code including instructions to (a) receive a patient analyte test result set, the patient the patient analyte test result set including an analyte value for a plurality of analytes; (b) generate a patient analyte level set from the patient analyte test result set and a first database, the first database maintaining analyte data information for a plurality of analytes and including an analyte record for each one of the plurality of analytes, each analyte record including an analyte low value, an analyte high value and an analyte mode value indicative of a statistical analysis of analyte values obtained from testing a human test group, the patient analyte level set including a patient analyte level for each analyte in the analyte test result set; (c) compare the patient analyte level set to a second database, the second database maintaining vitamin/nutrient information for a plurality of vitamins/nutrients and including a vitamin/nutrient record for each one of the plurality of vitamins/nutrients, each vitamin/nutrient record including a set of analytes associated with the particular vitamin/nutrient and an effect the particular vitamin/nutrient has on the associated analytes; and (d) determine a group of vitamins/nutrients that has supportive effects on the patient analyte levels.

27. A computer program embodied on a computer-readable medium as set forth in claim 26, wherein the instructions to generate the patient analyte level set comprise instructions to generate a patient percent status set, the patient percent status set including a value for each of the plurality of analytes in the patient analyte test result set.

28. A computer program embodied on a computer-readable medium as set forth in claim 27, wherein the instructions to generate the patient percent status set comprise instructions to calculate a percent status value for each element of the patient percent status set using the following:

if the patient analyte test result value is greater than the analyte mode value then percent status=50*(patient analyte test result value−analyte mode value)/(analyte high value−analyte mode value)

and, if the patient analyte test result value is less than the analyte mode value then percent status=50*(patient analyte test result value−analyte mode value)/(analyte mode value—analyte low value).

29. A computer program embodied on a computer-readable medium as set forth in claim 28, wherein the instructions to generate the patient analyte level set further comprise instructions to compare the patient percent status set to a preselected high status value and a preselected low status value.

30. A computer program embodied on a computer-readable medium as set forth in claim 29, wherein the preselected high status value is 25 and the preselected low status value is −25.

31. A computer program embodied on a computer-readable medium as set forth in claim 30, wherein the instructions to generate the patient analyte level set further comprise instructions to label the analyte level for each element of the patient analyte level set LOW if corresponding elements of the patient percent status set are less than or equal to −25, label the analyte level for each element of the patient analyte level set NORMAL if corresponding elements of the patient percent status set are greater than −25 and less than 25, and label the analyte level for each element of the patient analyte level set HIGH if corresponding elements of the patient percent status set are greater than or equal to 25.

32. A computer program embodied on a computer-readable medium as set forth in claim 31, wherein the instructions to generate the patient analyte level set comprise instructions to generate a normal limit value set for each of the plurality of analytes.

33. A computer program embodied on a computer-readable medium as set forth in claim 32, wherein the normal limit value set includes a high normal limit value and a low normal limit value.

34. A computer program embodied on a computer-readable medium as set forth in claim 33, wherein the high normal limit value is given by the equation high normal limit value=analyte mode value+(normal percent range)*(analyte high value−analyte mode value)

and the low normal limit value is given by the equation, low normal limit value=analyte mode value−(normal percent range)*(analyte mode value−analyte low value), wherein the normal percent range being a preselected value between 0 and 1.

35. A computer program embodied on a computer-readable medium as set forth in claim 34, wherein the instructions to generate the patient analyte level set further comprise instructions to label the elements of the patient analyte level set LOW if the corresponding elements of the patient analyte test result set are less than the low normal limit value, label the elements of the patient analyte level set NORMAL if the corresponding elements of the patient analyte test result set are greater than the low normal limit value and less than the high normal limit value, and label the elements of the patient analyte level set HIGH if the corresponding elements of the patient analyte test result set are greater than the high normal limit value.

* * * * *